(12) United States Patent
Covey et al.

(10) Patent No.: US 9,733,215 B2
(45) Date of Patent: *Aug. 15, 2017

(54) CONTAMINATION FILTER FOR MASS SPECTROMETER

(71) Applicant: DH TECHNOLOGIES DEVELOPMENT PTE. LTD., Singapore (SG)

(72) Inventors: Thomas R. Covey, Richmond Hill (CA); Bradley B. Schneider, Bradford (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/378,957

(22) Filed: Dec. 14, 2016

(65) Prior Publication Data

US 2017/0122908 A1 May 4, 2017

Related U.S. Application Data

(63) Continuation of application No. 14/894,494, filed as application No. PCT/IB2014/001143 on Jun. 20, 2014, now Pat. No. 9,564,302.

(60) Provisional application No. 61/838,185, filed on Jun. 21, 2013, provisional application No. 62/014,657, filed on Jun. 19, 2014.

(51) Int. Cl.
*H01J 49/00* (2006.01)
*H01J 49/16* (2006.01)
*H01J 49/14* (2006.01)
*G01N 27/62* (2006.01)
*H01J 49/04* (2006.01)

(52) U.S. Cl.
CPC ........ *G01N 27/624* (2013.01); *H01J 49/0031* (2013.01); *H01J 49/0422* (2013.01); *H01J 49/145* (2013.01); *H01J 49/165* (2013.01)

(58) Field of Classification Search
CPC ...... H01J 49/0031; H01J 49/34; H01J 49/145; H01J 49/165; H01J 49/004
See application file for complete search history.

(56) References Cited

U.S. PATENT DOCUMENTS

| | | | |
|---|---|---|---|
| 2008/0128609 A1* | 6/2008 | Miller | G01N 27/622 250/282 |
| 2009/0152455 A1* | 6/2009 | Wang | G06K 9/00496 250/252.1 |
| 2010/0207022 A1* | 8/2010 | Tang | G01N 27/624 250/282 |
| 2010/0213366 A1* | 8/2010 | Fernandez De La Mora | H01J 49/004 250/282 |

(Continued)

*Primary Examiner* — Nicole Ippolito
*Assistant Examiner* — Sean Luck
(74) *Attorney, Agent, or Firm* — John R. Kasha; Kelly L. Kasha; Kasha Law LLC

(57) ABSTRACT

Methods and systems for performing mass spectrometry are provided herein. In accordance with various aspects of the applicants' teachings, the methods and systems can utilize an ion mobility spectrometer operating at atmospheric or low-vacuum pressure to remove the major contributors to the contamination and degradation of critical downstream components of a mass spectrometer located within a high-vacuum system (e.g., ion optics, mass filters, detectors), with limited signal loss.

8 Claims, 19 Drawing Sheets

(56) References Cited

U.S. PATENT DOCUMENTS

| | | | |
|---|---|---|---|
| 2011/0101214 A1* | 5/2011 | Miller | G01N 27/624 250/282 |
| 2011/0127419 A1* | 6/2011 | Thomson | H01J 49/004 250/282 |
| 2011/0183431 A1* | 7/2011 | Covey | G01N 27/624 436/173 |
| 2011/0253890 A1* | 10/2011 | Belford | G01N 27/624 250/288 |

* cited by examiner

CONTAMINATION FILTER FOR MASS SPECTROMETER

RELATED APPLICATIONS

This application is a continuation of U.S. patent application Ser. No. 14/894,494, filed Nov. 27, 2015, filed as Application No. PCT/IB2014/001143 on Jun. 20, 2014, which claims priority to U.S. Provisional Patent Application No. 61/838,185, filed on Jun. 21, 2013, and U.S. Provisional Patent Application No. 62/014,657, filed on Jun. 19, 2014, the disclosures of which are incorporated by reference herein in their entireties.

FIELD

The invention generally relates to mass spectrometry, and more particularly to methods and apparatus utilizing an ion mobility spectrometer to remove contamination and prevent degradation of downstream components of a mass spectrometer operating in a high-vacuum chamber.

INTRODUCTION

Mass spectrometry (MS) is an analytical technique for determining the elemental composition of test substances with both qualitative and quantitative applications. For example, MS can be useful for identifying unknown compounds, determining the isotopic composition of elements in a molecule, determining the structure of a particular compound by observing its fragmentation, and quantifying the amount of a particular compound in a sample. Mass spectrometers have been widely used in the fields of chemistry and physics for over a century, and increasingly in biology over the past several decades. Sub-disciplines such as environmental monitoring for pollutants, forensic analysis for drugs of abuse and toxins, biomedical research, clinical disease diagnostics, food analysis, material science, and others, have been utilizing atmospheric pressure ionization mass spectrometers toward great practical value and to help achieve significant advancements in these fields. Large numbers of highly complex samples have been interrogated for the identity and quantity of a variety of chemical constituents at levels as low as parts per trillion.

As a result, mass spectrometry instrumentation has evolved toward increased selectivity as mass spectrometric detection and quantification of analytes contained within complex matrices generally requires high resolution separation techniques to reduce the effect of interfering species within the sample. Despite advances in MS that have enabled high-resolution mass analyzers to distinguish target species from interfering species within about 0.01 Th, it is not always feasible or possible to use a high-resolution mass analyzer to separate interfering species, for example, due to availability, cost, and/or experimental conditions.

Accordingly, various approaches for increasing the resolution of analytes have been developed including, for example, improved sample preparation techniques prior to ionization such as liquid chromatography, derivatization prior to LC separation, solid-phase extraction, or turbulent-flow chromatography. Additionally, various techniques have been developed to separate charged species within an ionized sample based on characteristics beyond mass-to-charge ratio (m/z). By way of example, whereas MS generally analyzes ions based on differences in m/z, ion mobility spectrometry (IMS) and other ion mobility separation techniques (e.g., differential mobility spectrometry (DMS), high field asymmetric waveform ion mobility spectrometry (FAIMS), Field Ion Spectrometry (FIS)) instead separate ions based upon other factors such as size, shape, and charge state as ions drift through a gas (typically at atmospheric pressure) in an electric field. The drift time through an electrostatic field is characteristic of the mobility of the ion (e.g., its size and shape and its interactions with the background gas), or in the case of DMS and FAIMS devices, the compensation voltage (CV or CoV) required to preferentially prevent the drift of a particular species is characteristic of its differential mobility. However, operating parameters for ion mobility spectrometers, however, are conventionally configured to optimize the resolution of the various charged species generated from the sample (e.g., to separate isobaric species), often at the expense of decreased transmission of ions of interest. Moreover, the effects of ion mobility conditions on particular species can be unpredictable and often lead to ion loss (i.e., decreased signal/sensitivity).

Additionally, the ion optics and other mass analyzer components, which are located deep inside high-vacuum chambers where ion trajectories can be precisely controlled by electric fields, are delicate and prone to fouling by the excessive sample loads and debris generated by atmospheric pressure ion sources. While, ionization at atmospheric pressure, whether by chemical ionization processes or by electrospray, is generally a highly efficient means of generating ions and microamps of ion current of the analyte(s) of interest, contaminating/interfering ions can also be created in high abundance at ion current levels far in excess of the analyte(s) of interest. The undesirable transport of contaminating ions and charged particles from the atmospheric pressure source region to the high-vacuum chamber of a mass spectrometer can also result in contamination of ion optics within the intermediate pumping stages of a differentially pumped mass spectrometer. Such contamination can not only interfere with the mass spectrometric analysis, but also lead to increased costs or decreased throughput necessitated by the cleaning of critical components within the high-vacuum chamber and intermediate pressure regions. Because of the higher sample loads and contaminating nature of the biologically based samples being analyzed with current day atmospheric pressure ionization sources, reduction of system contamination remains a critical concern.

The concept of using a differential ion mobility (DMS) device as a pre-filter to a mass spectrometer (MS) has been developed by several groups. This includes the use of high field asymmetric waveform ion mobility spectrometers (FAIMS) which operate on the same principles of utilizing the difference in ions high and low field mobility to effect separations. The expressed purpose for coupling DMS with MS has been to increase the selectivity of the mass spectrometer by providing a high resolution ion mobility device that can separate ion species that a mass spectrometer cannot, thus increasing the specificity of the system by hyphenating two instruments that separate ions on different principles, i.e. the mobility and mass measurements are orthogonal to each other (Schneider et al, Int. J. Ion Mobility Spec., 2013, 16, 207-216). The separation of isobaric species is an example of something a DMS device can do in many cases but a mass spectrometer cannot. Compounds with different primary, secondary, or tertiary structures having the same mass (isobaric) have been shown to separate with differential ion mobility thereby improving the selectivity of the mass spectrometer when used in combination with such a device. Also, isobaric compounds with different gas phase ion chemistries can be separated by DMS adding further resolving power to the mass spectrometer. As such, the focus on the design of such mobility systems has been toward the improvement of the resolution and peak capacity. Resolution (Rs) is defined in equation 1 as:

$$Rs = \frac{CoV}{FWHM} \quad \text{(Equation 1)}$$

where CoV represents the compensation voltage required to pass a specific ion through the cell and FWHM is the full width half maximum in Volts of the peak generated during a scan of the CoV. Resolution, as defined here, provides an indication of the CoV shift and differential mobility peak width for a single compound.

Peak capacity (Pc) is defined as:

$$Pc = CoV \text{ range}/FWHM \quad \text{(Equation 2)}$$

where CoV range is the compensation range in Volts over which a large number of compounds is spread and FWHM is the average full width half maximum in Volts of the peaks generated during a scan of the CoV for a large number of compounds. The peak capacity is an indicator of the number of compounds that can be separated in a complex mixture.

A third important performance characteristic of a DMS cell is the efficiency with which it transmits ions though the mobility analyzer defined as:

$$Te = Sd/S \quad \text{(Equation 3)}$$

where Te is the ion transmission efficiency, Sd is the number of ions measured by the mass spectrometer detector with the DMS filter installed and filtering and S is the number of ions measured by the mass spectrometer detector with no DMS filter installed on the mass spectrometer. Transmission efficiency indicates how many ions are lost in the DMS cell.

Transmission efficiency tends to run counter to both resolution and peak capacity. That is in order to maximize resolution and peak capacity, the transmission efficiency is compromised. As mentioned above, the current thinking in the field of differential ion mobility instrumentation is to maximize selectivity, i.e. resolution and peak capacity. An example of this is illustrated in the designs of Shvartsburg (Shvartsburg, A. A.; Smith, R. D. 2013. *"Separation of protein conformers by differential ion mobility in hydrogen rich gases"* Anal. Chem. 85, 6967-6973) which set the current record for DMS devices achieving resolution values of about 400-500.

For purposes of illustration, refer to FIG. 3 which defines the important parameters of the cell dimensions. FIG. 3 shows a schematic of a rectangular, planar DMS sensor. The separation occurs in the gap bounded by the electrodes where the RF field is applied. Cell dimensions and power supply specifications can take on a wide variety of dimensions and values depending on the applications and specifications targeted. One typical set of specifications for a high resolution device are 1 mm gap height, 30 mm length, and 10 mm width powered with a 3 MHz RF asymmetric waveform generator having a typical maximum output of 3000 V 0-peak.

FIG. 4A shows a schematic of a stand-alone DMS sensor. The ion filter region is comprised of two planar, parallel electrodes. Faraday plates at the exit serve as the detector for positive and negative ions simultaneously. FIG. 4B shows a schematic of a DMS with a mass spectrometer as the ion detector and depiction of the asymmetric waveform, where the integrated time/voltage areas under the low and high field portions within each period are the same. The RF waveform is drawn as an idealized square wave but not all DMS power supplies are designed to deliver square wave functions for practical reasons related to power consumption. The amplitude of the waveform is referred to as the separation voltage (SV). The compensation voltage (CoV) is a DC potential applied to an electrode used to counteract the ion's migration toward an electrode in response to the SV, its magnitude is proportional to the ion's differential mobility. It is shown as a voltage ramp here, but can be set to a fixed value to allow targeted ions to pass through the DMS, while excluding non-targeted ions. For illustration purposes, the DMS of FIG. 4B is shown in front of the mass spectrometer inlet with no additional sealing means. In practice, ion transmission from the DMS cell to the mass spectrometer is usually maximized by providing sealing means.

FIG. 5 shows more details of a DMS-MS system. The design of the DMS cell involves balancing the various dimensions of length, width, gap height, gas velocity, RF frequency, amplitude, and waveform shape to achieve the desired performance specifications tailored to a specific application. The time an ion spends inside the cell is of particular importance with regards to the ultimate resolution, peak capacity, and transmission efficiency. This is referred to as the flight time or equivalently the residence time. The flight time ($\tau$) can be calculated from Equation 4:

$$\tau = \frac{lwh}{Q} \quad \text{(Equation 4)}$$

where l, w, h, and Q are the sensor length, width, height, and volumetric gas flow, respectively.

FIG. 5 shows a DMS coupled to a mass spectrometer where the maximum transport gas flow rate is determined by the vacuum drag of the MS and can be reduced in a controlled manner by a variable leak, referred to as the throttle gas, used to adjust resolution. The throttle gas can also be reversed to draw thereby increasing the velocity of the transport gas beyond that provided by the vacuum system. This feature would reduce resolution and improve ion transmission. This approach for DMS coupling is the subject of Applicants' U.S. Pat. Nos. 8,084,736 and 8,513,600 herein incorporated by reference. The curtain gas supplies both the transport gas and counter current flow which keeps uncharged atmospheric contaminants out of the transport gas.

All aspects of the design of a DMS cell are parametric, i.e. they are highly interdependent. There is no particular dimension, ratio of dimensions, or RF frequency, amplitude, or waveform that can be expected to provide optimal performance for the primary figures of merit simultaneously, those figures of merit being resolution, peak capacity, and ion transmission efficiency (sensitivity). The design of the cell and its power supplies will accentuate some of these figures of merit while at the same time compromising others. A clear understanding of the desired application is required to define the performance specification for each of these figures of merit, which then will establish the general direction of the design of the cell. To date, the evolution of DMS instrumentation has been toward improvements in resolution and peak capacity.

Three examples of altering various aspects of the design of a particular cell and the effect that has on the performance characteristics of resolution, peak capacity, and transmission will follow to serve as examples. The cell used in these examples had dimensions of 1×10×30 mm for gap height, width, and length, respectively, with the alterations as described. The general trends that the performance characteristics display as the design is altered in the fashion described in these examples would be similar regardless of what other specific geometries or power supply specifications were to be used.

FIGS. 6A and 6B are examples of the improvement in the resolution of a DMS device by optimizing the design to increase the flight time described by Schneider B B, Nazarov E G, Covey T R., "Peak Capacity in Differential Mobility Spectrometry: Effects of Transport Gas and Gas Modifiers", Int. J. Ion Mobil. Spectrom., 2012a, 15, 141-150. FIGS. 6A and 6B show ionograms of a six component mixture of drugs showing the effect of residence time on resolution in a DMS coupled to a mass spectrometer. The term ionogram was coined to describe this form of data acquisition where the CoV is scanned at a constant SV, while a sample is introduced over the time frame of the scan (Guevremont R., "High-Field Asymmetric Waveform Ion Mobility Spectrometry: A New Tool for Mass Spectrometry", J. Chrom. A., 2004, 1058, 3-19). The intensities of the signals from the components of the sample are recorded during the scan and the resolution and peak capacity of the separation can be determined. FIG. 6A has a 6.5 ms residence time. FIG. 6B has a 20 ms residence time. Residence time can be controlled by several means including altering the transport gas flow rate and/or the dimensions of the cell. The sample was composed of 1) phenylalanine, 2) histidine, 3) methylhistamine, 4) minoxidil, 5) cimetidine, and 6) perphenazine, infused into an electrospray ion source at 10 μL/min. The signal was monitored for each component by multiple reaction monitoring (MRM) on a triple quadrupole MS. Increasing the flight time provides a narrowing of the observed mobility peaks, but does not change the CoV. Improved resolution is observed with increasing flight time; however the peak intensity decreases as a result of increased ion losses due to diffusion processes in the mobility analyzer.

FIGS. 7A-7D show examples of the changes in the peak capacity of a DMS device resulting from altering the gap height over a range of a) 0.25 mm, b) 0.50 mm, c) 1 mm, and d) 1.5 mm. As described in Equation 2, peak capacity, for a particular separation, is defined as the ratio of the CoV range over which the specified compound set is spread divided by the FWHM of individual peaks. The measured CoV for a given compound scales with the gap height. However, the limiting peak width for the 4 DMS sensors used to generate these data was similar. Therefore, the peak capacity improved with increased gap height, predominantly because the range of CoV voltages over which this compound set was spread increased substantially more than the average FWHM. The peak capacities ranged from 10.5 to 38.5 for the smallest to the largest gap height sensors, respectively.

The improvement in transmission efficiency for methylhistamine ions (1×10×30 mm cell dimensions) as the separation voltage increased is seen in FIG. 8. Ionograms are shown at three different separation voltages demonstrating increasing ion signal with increasing SV. The upper limits to the SV are determined by other aspects of the cell geometry, in particular gap height. A practical limit is reached when the field between the cells (V/mm) reaches the discharge limit causing a breakdown of the transport gas and electrical arcing between the electrodes.

The above three examples illustrate some of the effects on the performance characteristics of resolution, peak capacity, and ion transmission efficiency that the key design elements of separation voltage, gap height, and ion flight time affect. Although the data were obtained with specific geometries and power supplies, the trends can be generalized to any particular DMS or FAIMS design. As mentioned earlier, the current status in the development of DMS-MS devices by both commercial and non-commercial researchers has been in the direction of improvements to resolution and peak capacity as the first consideration. Transmission efficiency is also considered, but it plays a secondary role to the optimization of selectivity.

Accordingly, there remains a need for methods and systems that enable the analysis of increasingly complex samples with improved sensitivity, while reducing potential sources for contamination.

SUMMARY

The present teachings are based on the unexpected discovery that the use of ionization sources operating at atmospheric pressure (e.g., electrospray and chemical ionization sources) can lead to the formation of high mass ions (e.g., charged solvent clusters) that can pass through interface regions that include counter-current gas flows (curtain gas) and contaminate the optics of an ion spectrometer as well as severely degrade the signal-to-noise ratio, for example, by generating large signal transients. In some cases, these high mass ions can have a mass greater than about 2000 amu, e.g., in a range of about 2000 amu up to and greater than 2,000,000 amu. It has additionally been discovered that an ion mobility spectrometer can be configured to filter out these high mass ions while ensuring that a substantial portion of the charged species of interest (e.g., at least about 50%, or at least about 70%, or at least about 90%) pass through the ion mobility spectrometer for analysis by a downstream mass analyzer.

The present teachings are based on the unexpected discovery that a high transmission, low resolution ion mobility spectrometer device can filter the high mass ions or charged debris to keep the vacuum system of a mass spectrometer clean for long periods of time. The device configuration takes into account the residence time of the ions through the ion mobility spectrometer, the gap height between the electrodes of the ion mobility spectrometer, and the maximum separation voltage applied to the electrodes of the ion mobility spectrometer, wherein a ratio of the residence time of the ions through the ion mobility spectrometer to the product of gap height between the electrodes of the ion mobility spectrometer and the maximum separation voltage applied to the electrodes of the ion mobility spectrometer being less than 0.002. In various aspects, a ratio of the residence time of the ions through the ion mobility spectrometer to the product of gap height between the electrodes of the ion mobility spectrometer and the maximum separation voltage applied to the electrodes of the ion mobility spectrometer being less than 0.0015.

Accordingly, in various aspects, certain embodiments of the Applicants' teachings relate to a method of operating a mass spectrometer system, the method comprising providing an ion source for ionizing a sample to generate a plurality of ions, providing a low resolution, high transmission ion mobility spectrometer for reducing contamination, introducing said plurality of ions into an input end of the ion mobility spectrometer, transporting said plurality of ions in a drift gas through the ion mobility spectrometer from the input end to an output end thereof, providing a mass spectrometer in fluid communication with the differential mobility spectrometer for receiving the ions from the output end of differential mobility spectrometer, and a ratio of the residence time of the ions through the ion mobility spectrometer to the product of gap height between electrodes of the ion mobility spectrometer and the maximum separation voltage applied to the electrodes of the ion mobility spectrometer being less than 0.002. In various aspects, a ratio of the residence time of the ions through the ion mobility spectrometer to the product of gap height between the electrodes of the ion mobility spectrometer and the maximum separation voltage applied to the electrodes of the ion mobility spectrometer being less than 0.0015.

In various aspects, the residence time of the ions can be less than 100 ms. In various aspects, the gap height can be between 0.02 and 5 millimeters. In various aspects, the SV comprises an RF signal applied to the electrodes, and including a CoV comprised of a DC signal applied to the electrodes, and wherein the RF and DC signals are configured to generate a fringing field in proximity of said input end of the ion mobility spectrometer effective to cause said ions having a selected mass to follow off-axis trajectories to collide with said electrodes in proximity to said input end. In various aspects, the method further comprises selecting a transit time of the ions through the ion mobility spectrometer to facilitate transit of analytes of interest through the ion mobility spectrometer. In various aspects, the transit time can be selected to provide transmission efficiency of greater than 50% for a broad mass range of ions. In various aspects, the ion mobility spectrometer comprises a differential mobility spectrometer or a FAIMS system.

In various aspects, certain embodiments of the Applicants' teachings relate to a system for analyzing ions comprising an ion source, a low resolution, high transmission ion mobility spectrometer for reducing contamination having an input end for receiving ions from source and an output end, the ion mobility spectrometer having an internal operating pressure, electrodes, and at least one voltage source for providing DC and RF voltages to the electrodes, a mass spectrometer in fluid communication with the differential mobility spectrometer for receiving the ions from the output end of differential mobility spectrometer, a controller operably coupled to the ion mobility spectrometer and configured to control the DC and RF voltages; and a ratio of the residence time of the ions through the ion mobility spectrometer to the product of gap height between electrodes of the ion mobility spectrometer and the maximum separation voltage applied to the electrodes of the ion mobility spectrometer being less than 0.002. In various aspects, a ratio of the residence time of the ions through the ion mobility spectrometer to the product of gap height between the electrodes of the ion mobility spectrometer and the maximum separation voltage applied to the electrodes of the ion mobility spectrometer being less than 0.0015.

In various aspects, the residence time of the ions can be less than 100 milliseconds. In various aspects, the gap height can be between 0.02 and 5 millimeters. In various aspects, the separation voltage (SV) comprises an RF signal applied to the electrodes, and including a compensation voltage (CoV) comprised of a DC signal applied to the electrodes, and wherein the RF and DC signals are configured to generate a fringing field in proximity of said input end of the ion mobility spectrometer effective to cause said ions having a selected mass to follow off-axis trajectories to collide with said electrodes in proximity to said input end. In various aspects, the system further comprises selecting a transit time of the ions through the ion mobility spectrometer to facilitate transit of analytes of interest through the ion mobility spectrometer. In various aspects, the transit time can be selected to provide transmission efficiency of greater than 50% for a broad mass range of ions. In various aspects, the ion mobility spectrometer comprises a differential mobility spectrometer or a FAIMS system.

In some embodiments, the ion mobility spectrometer can also be configured to filter out not only the above-described high mass ions, but also ions having an m/z less than a threshold (e.g., 100, 150, or 200 amu), also referred to herein as low-mass ions. Such low mass ions can be created in high abundance due to the large number of molecules subjected to ionization at atmospheric pressures (e.g., in the presence of ambient molecules within the atmospheric or near-atmospheric chamber). For example, in some cases, when liquid samples are introduced into an atmospheric pressure ion source, the solvent molecules can produce ion current levels far in excess of the ion current associated with the analyte(s) of interest in the sample. The removal of such unwanted low-mass ions can, for example, improve the signal-to-noise provided by a downstream mass analyzer.

Accordingly, the methods and systems described herein can be effective to reduce the amount of unwanted charged material from entering the vacuum system, thereby maintaining peak performance of the mass spectrometer systems over longer periods of time and during heavy use. While the operating parameters of ion mobility spectrometers are conventionally configured to maximize resolution (e.g., to separate isobaric species while maintaining sufficient signal to resolve peaks), the present teachings are based in part on the discovery that an ion mobility spectrometer can be configured to operate in a low resolution mode, e.g., operating at a high transmission efficiency with broad peaks to maximize the transit of the species of interest through the spectrometer and thereby improve sensitivity, while nonetheless filtering out high mass and low mass species. In some embodiments, the methods and systems according to the present teachings can be employed to remove up to about 99% of unwanted ions generated by the ion source, while allowing the ions of interest to pass to a downstream mass analyzer.

In accordance with various aspects, certain embodiments of the applicants' teachings relate to a method of operating a mass spectrometer system including an ion mobility spectrometer (e.g., a differential mobility spectrometer or FAIMS) and a mass spectrometer in fluid communication with the ion mobility spectrometer. According to the method, a sample is ionized to generate a plurality of ions, which are introduced into an input end of the ion mobility spectrometer. As the plurality of ions are transported in a drift gas through the ion mobility spectrometer from the input end to an output end thereof, ions having a mass less than about 200 amu (e.g., less than about 150 amu or less than about 100 amu) and greater than about 2000 amu (e.g., in a range of about 2000 amu to about 2,000,000 amu) are filtered from the drift gas as the plurality of ions are transported within the ion mobility spectrometer. The method can also include introducing ions exiting the output end of the ion mobility spectrometer into the mass spectrometer.

In some aspects, the filtering steps can comprise diverting (e.g., deflecting) a portion of the ions to collide with at least one electrode of said ion mobility spectrometer. In various aspects, filtering ions or charged particles having a mass greater than about 2000 amu comprises applying an RF signal to electrodes of the ion mobility spectrometer, the RF signal having an amplitude and frequency configured to cause said ions having a mass greater than about 2000 amu to follow unstable trajectories.

In accordance with some aspects, the ion mobility spectrometer comprises at least a pair of electrodes having a separation voltage and a compensation voltage applied thereto, the method further comprising selecting a CoV such that a broad mass range of analytes are transported through the ion mobility spectrometer to exit through said output end thereof. For example, in some aspects, the combination of CoV and SV can comprise RF and DC signals applied to at least one of the electrodes configured to generate a fringing field in proximity of said input end of the ion mobility spectrometer effective to cause said ions having a mass greater than 2000 amu to follow off-axis trajectories to collide with said electrodes in proximity to said input end.

In various aspects, the transit time of the ions through the ion mobility spectrometer can be selected to facilitate transit of analytes of interest through the ion mobility spectrometer. For example, the transit time can be selected to provide transmission efficiency of greater than 50% or more for a broad mass range of ions. By way of example, the transit time can be less than about 7 ms, less than about 6 ms, less than about 5 ms, and less than about 2 ms, in various embodiments that include a 1 mm gap height between electrodes. In various embodiments, the transmit time may vary depending upon gap height or separation voltage. In some aspects, the transit time can be selected to minimize losses of ions within a selected mass or m/z range. For example, the transit time can be selected such that ions entering the input end of the ion mobility spectrometer and having a mass in the range of about 200 amu to about 2000 amu are preferentially transported to the output end of the ion mobility spectrometer. In related aspects, the ions having a mass in the range of about 200 amu to about 2000 amu can be substantially unresolved at the output end of the ion mobility spectrometer. In this manner, the differential ion mobility spectrometer operates in a broad band pass mode, rather than the ion resolving mode used in the prior art. In some aspects, the ion mobility spectrometer can be configured with gas flows and cell dimensions scaled to provide resolutions sufficiently low to provide transmission efficiencies greater than 50% for a broad mass range of interest.

In some embodiments, the gas flow rate through the ion mobility spectrometer can be selected to ensure that ions of interest transit through the spectrometer with minimal loss, if any, e.g., a loss of less than about 50%, less than about 20%, or less than about 10%, while the high mass and low mass ions are filtered out. In various aspects, the method can comprise selecting a flow rate of the drift gas through the ion mobility spectrometer such that the transit time is less than about 1 ms and providing transmission efficiencies greater than about 50% for a broad mass range. By way of example, the flow rate of the drift gas through the ion mobility spectrometer can be greater than about 5 L/min for providing efficiencies greater than about 50% for a broad mass range when using electrode dimensions of 1×10×30 mm.

In accordance with another aspect, certain embodiments of the applicants' teachings relate to a method of operating a mass spectrometer system including an ion mobility spectrometer and a mass spectrometer in fluid communication with the ion mobility spectrometer. According to the method, a sample can be ionized to generate a plurality of charged species and the charged species can be introduced into an input end of the ion mobility spectrometer. Ions of said charged species having a mass in a range from about 200 amu to about 2000 amu can be preferentially transported to an output end of the ion mobility spectrometer, the gas flows and cell dimensions of the operating ion mobility spectrometer (e.g., non-zero DC and/or RF voltages being applied thereto) being configured to provide transmission efficiencies greater than 50% for a broad mass range.

In accordance with some aspects, certain embodiments of the applicants' teachings relate to a system for analyzing ions comprising an ion source (e.g., an atmospheric pressure ion source) and an ion mobility spectrometer having an input end for receiving ions from the ion source and an output end, the ion mobility spectrometer having an internal operating pressure, electrodes, and at least one voltage source for providing DC and RF voltages to the electrodes. The system further includes a mass spectrometer in fluid communication with the differential mobility spectrometer for receiving the ions from the output end of the differential mobility spectrometer. A controller can be operably coupled to the ion mobility spectrometer and configured to control the DC and RF voltages such that the ion mobility spectrometer preferentially transports ions having a mass in a range from about 200 amu to about 2000 amu to the output end of the ion mobility spectrometer. In some aspects, the controller can be configured to operate the ion mobility spectrometer with a transmission efficiency of greater than 50% for a broad mass range.

In some aspects, the controller can be configured to modulate the RF and DC potentials applied to the electrodes so as to generate a fringing field in proximity to the input end of the ion mobility spectrometer, the fringing field configured to filter ions having a mass greater than about 2000 amu (e.g., in a range of about 2000 amu to about 2,000,000 amu) or less than about 200 amu, from the ions received from the ion source. Alternatively or additionally, the controller can be configured to modulate the DC and RF potentials applied to the electrodes such that ions having a mass less than about 200 amu are filtered as the ions received from said source are transported through the ion mobility spectrometer.

In various aspects, a vacuum chamber can surround the mass spectrometer for maintaining the mass spectrometer at a vacuum pressure lower than the internal operating pressure of the ion mobility spectrometer, the vacuum chamber being operable to draw a drift gas flow including the ions through the differential mobility spectrometer and into the vacuum. Multiple differentially pumped vacuum stages, including ion transport optics may be disposed between the atmospheric pressure inlet and the high-vacuum region containing the mass analyzer. The system can additionally include a gas port for modifying a gas flow rate through the ion mobility spectrometer, the gas port being located between the ion mobility spectrometer and the mass spectrometer. In related aspects, the controller can be configured to modulate the gas flow rate through the ion mobility spectrometer and the at least one voltage source such that the ion mobility spectrometer can be modulated between a low-resolution mode in which the transmission efficiency is greater than 50% for a broad mass range of ions and a high-resolution mode in which ions can be resolved based on their mobility in the ion mobility spectrometer. In some aspects, the gas flow rate in the low-resolution mode is greater than the gas flow rate in the high-resolution mode. For example, the gas flow rate in the low-resolution mode can be greater than about 5 L/min. By way of example, the gas flow rate in the low-resolution mode can be scaled with the cell dimensions to provide a transmission efficiency greater than 50%.

In accordance with some aspects, certain embodiments of the applicants' teachings relate to a mass spectrometer system including a mass analyzer located in a high vacuum chamber for analyzing sample ions formed at atmospheric pressure and directed to the analyzer through an intermediate atmospheric pressure chamber. The intermediate atmospheric pressure chamber can include at least one pair of electrodes in opposition to each other defining a path through which the ions travel, said path including a region of defocusing electric fringe fields; means associated with the opposing electrodes for deflecting charged clusters and/or debris having an m/z greater than a first threshold within a gas stream entering an input end of the plurality of electrodes, the deflection preventing the charged clusters and/or debris from entering the high vacuum chamber; means associated with the opposing electrodes for deflecting unwanted ions having an m/z lower than a second threshold such that said ions of lower m/z are prevented from entering the high vacuum chamber; and means for providing a high volumetric gas flow through the plurality of electrodes, the gas flow being configured for transporting the ions to the mass spectrometer with minimal loss of ions in a m/z range between the lower m/z and the higher m/z.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way.

DETAILED DESCRIPTION

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

Methods and systems for performing mass spectrometry utilizing an ion mobility spectrometer are provided herein. In accordance with various aspects of the applicants' teachings, the methods and systems described herein can be effective to reduce the amount of unwanted charged material from entering the vacuum system by deflecting this charged material to non-critical surfaces located in the atmospheric region of the instrument, where they can be readily accessed, cleaned and/or replaced. In some aspects, intervals between maintenance of vacuum system components may be increased by at least an order of magnitude.

While the operating parameters of ion mobility spectrometers are conventionally configured to optimize resolution (e.g., by separating isobaric species), the present teachings provide an ion mobility spectrometer operating in a low resolution mode to optimize the transit of the species of interest through the spectrometer and thereby improve sensitivity, while filtering out unwanted high mass and low mass species.

Figure 1A:
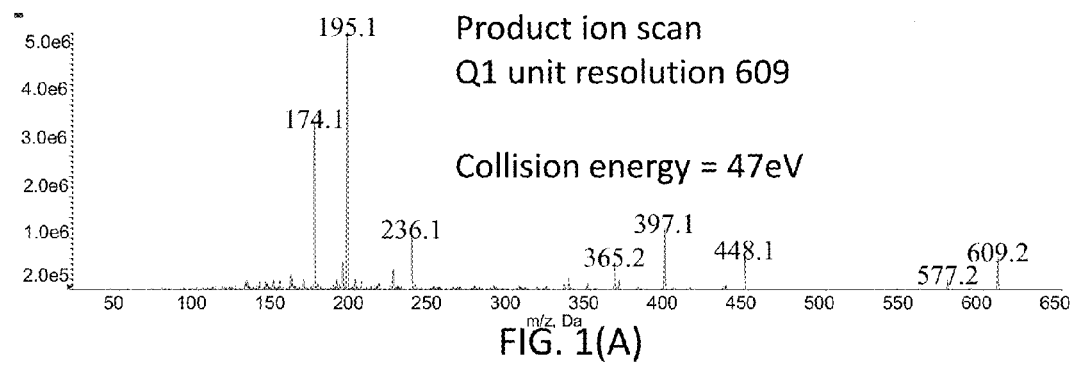
FIG. 1(A) depicts MS/MS data of a sample containing reserpine (609.2 m/z), with Q1 filtering ions less than about 1000 m/z and with the collision energy in Q2=47 eV.

As indicated above, the present teachings are based in part on the discovery that the use of ionization sources operating at atmospheric pressure (e.g., electrospray and chemical ionization sources) can lead to the formation of high mass ions (e.g., charged solvent clusters) that may pass through mass spectrometer inlets that include curtain gas protection. With reference now to FIG. 1(A), a product ion chromatogram is shown in which a sample containing 10 pg/uL of reserpine was subjected to atmospheric pressure ionization and run through MS/MS analysis (without utilizing a front-end ion mobility spectrometer in accordance with the present teachings) utilizing a QTRAP® 5500 system marketed by AB Sciex. The collision energy was 47 eV. Fragmentation of reserpine ions is observed, with a wealth of daughter ions, including m/z 174 and 195.

Figure 1B:
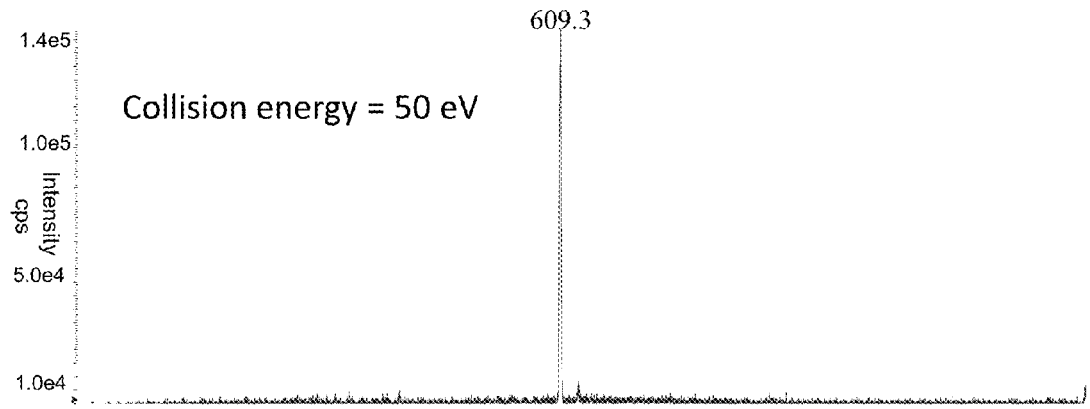
FIG. 1(B) depicts data from an "Asteroid scan" of a sample containing reserpine (609.2 m/z), with Q1 filtering ions less than about 1000 m/z and with the collision energy in Q2=50 eV.
Figure 1C:
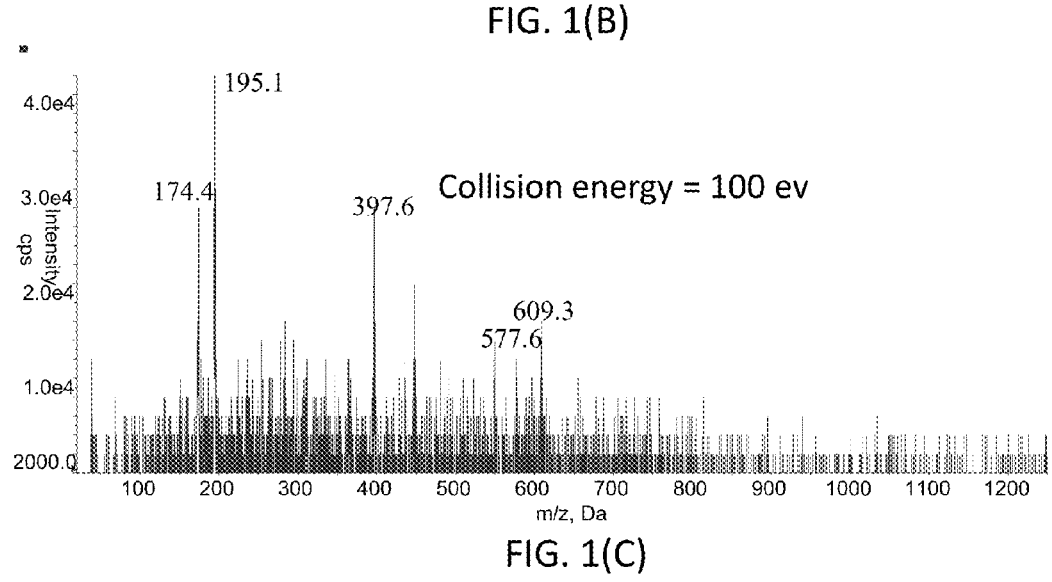
FIG. 1(C) depicts data from an "Asteroid scan" of a sample containing reserpine (609.2 m/z), with Q1 filtering ions less than about 1000 m/z and with the collision energy in Q2=100 eV.

FIGS. 1(B) and 1(C) demonstrate results of an experiment where Q1 was configured to open resolution at m/z 1250 such that ions at an m/z less than about 1000 were filtered. The remaining ions and charged particles were transported to Q3 and subjected to collision energies ramped from 0 eV to 150 eV as the spectra of the product ions were detected. As expected, at 0 eV, no ion signal was observed as the reserpine ions are below the filter threshold (XIC not shown). However, as the collision energy increases, the product ion scan indicates the presence of several peaks characteristic of both reserpine precursor ions (609.2 m/z) as well as common product ions (e.g., 195.1 m/z) of reserpine. Without being bound by any particular theory, the presence of these peaks is believed to demonstrate that although Q1 was set to filter reserpine precursor ions and other ions having m/z less than about 1000, precursor reserpine ions nonetheless entered Q2 as part of a massive charged residue. Such charged residues formed during electrospray ionization of high concentration samples incorporate a large amount of mass beyond the mass range of mass spectrometers (i.e., the reason why no signal was observed at 0 eV), and as will be appreciated by a person skilled in the art in light of the present teachings. The presence of such high mass charged residues might not only degrade the signal-to-noise ratio, for example, by generating unwanted, unexpected, or interfering product ions, but could also contaminate critical components within the vacuum chamber housing the mass analyzer components or ion optics. FIGS. 1(B) and 1(C) show results using collision energies of 50 eV and 100 eV, respectively. Because most biological samples (e.g., blood plasma) include high concentrations of background matrix material that could co-elute with an analyte of interest from an LC column and generate high mass charged residues that would follow the same field lines as the ions of interest, the residues from these samples could be observed as large signal transients as they hit the electron multiplier detector, thereby creating noise spikes that severely degrade signal to noise measurements. This is particularly problematic with analogue detection circuits because each individual residue carries thousands of charges. Since this material has the ability to penetrate deep into the ion optics of the mass spectrometer by virtue of its charge, it is a major source of serious ion optic contamination and performance loss.

In some cases, these high mass ions can have a mass greater than about 2000 amu, e.g., in a range of about 2000 amu up to and greater than 2,000,000 amu. As discussed below, the present teachings provide an ion mobility spectrometer configured to filter out these high mass ions while ensuring that a substantial portion of the charged species of interest (e.g., at least about 50%, or at least about 70%, or at least about 90%) pass through the ion mobility spectrometer for analysis by a downstream mass analyzer.

Additionally, in accord with various aspects of the present teachings, the ion mobility spectrometer can be configured to filter out not only the above-described high mass ions, but also ions having an m/z less than a threshold (e.g., 100, 150, or 200 amu). Such low mass ions can be created in high abundance due to the large number of molecules subjected to ionization at atmospheric pressure (e.g., in the presence of ambient molecules within the atmospheric or near-atmospheric chamber). For example, in some cases, when liquid samples are introduced into an atmospheric pressure ion source, the solvent molecules can produce ion current levels far in excess of the ion current associated with the analyte(s) of interest in the sample. The removal of such unwanted low-mass ions can, for example, improve the signal-to-noise provided by a downstream mass analyzer.

While the operating parameters of ion mobility spectrometers are conventionally configured to optimize the resolution provided by the spectrometer (e.g., to separate isobaric species), the present teachings provide an ion mobility spectrometer configured to operate in a low resolution mode, e.g., operating at a resolution sufficiently low to provide transmission efficiencies of greater than 50% for a broad mass range through the spectrometer and thereby improve sensitivity, while filtering out high mass and low mass species. In various embodiments, the methods and systems according to the present teachings can be employed to remove up to about 99% of unwanted ions generated by the ion source, while allowing the ions of interest to pass to a downstream mass analyzer.

Figure 2:
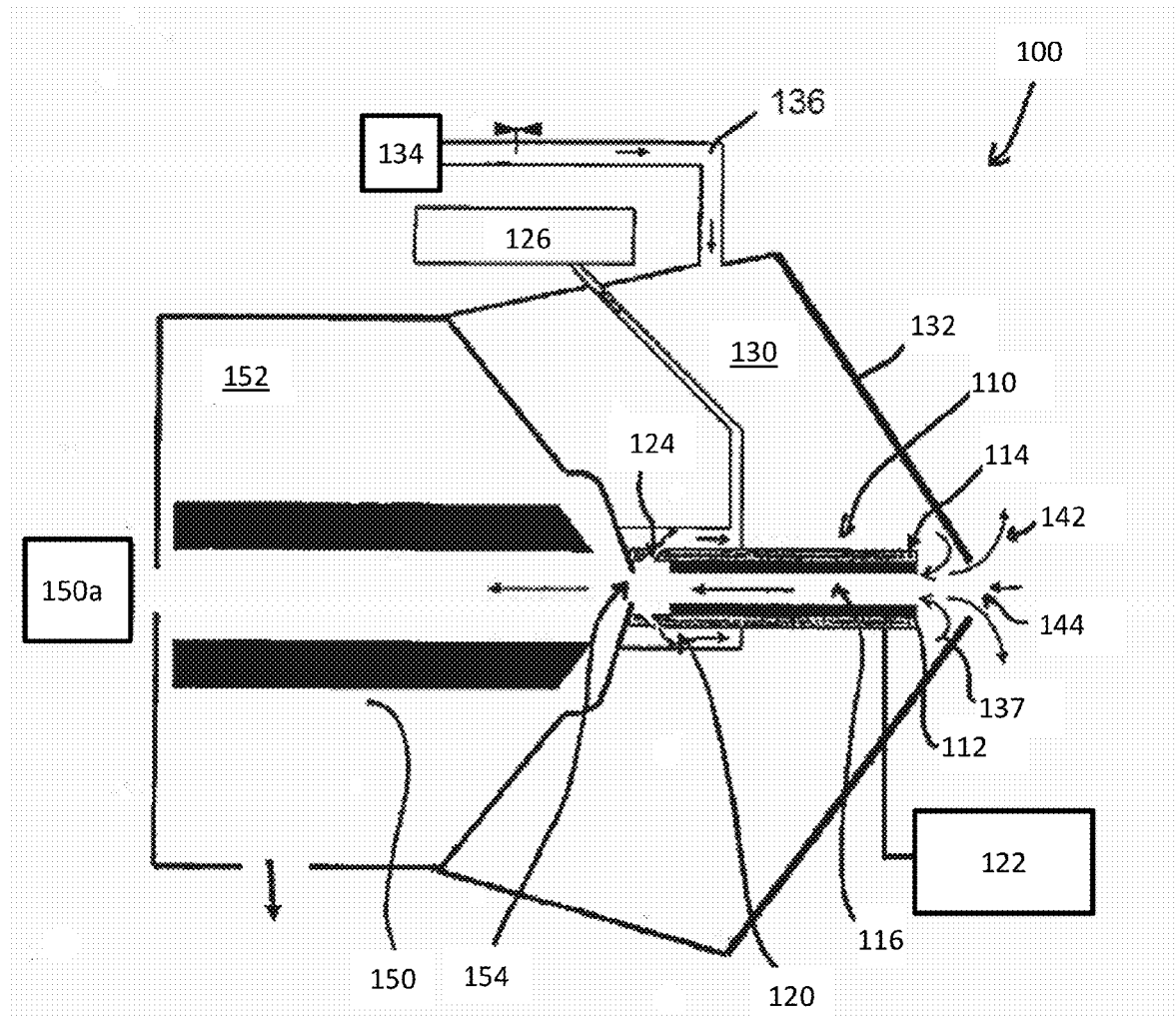
FIG. 2, in a schematic diagram, illustrates an exemplary mass spectrometry system including a differential mobility spectrometer in accordance with various aspects of the applicants' teachings.

With reference now to FIG. 2, an exemplary ion mobility spectrometer/mass spectrometer system 100 in accordance with various aspects of Applicants' teachings is illustrated schematically. As shown in FIG. 2, the ion mobility spectrometer/mass spectrometer system 100 generally comprises a differential mobility spectrometer 110 in fluid communication with a first vacuum lens element 150 of a mass spectrometer (hereinafter generally designated mass spectrometer 150). As will be appreciated by a person skilled in the art, the ion mobility spectrometer/mass spectrometer system 100 represents only one possible configuration for use in accordance with various aspects of the systems, devices, and methods described herein. The mobility spectrometer 110 can have a variety of configurations, but is generally configured to resolve ions based on their mobility through a fixed or variable electric field. For example, the mobility spectrometer can be any of an ion mobility spectrometer, a differential mobility spectrometer, or FAIMS devices of various geometries such as parallel plate, curved electrode, or cylindrical FAIMS device, among others.

In the exemplary embodiment depicted in FIG. 2, the differential mobility spectrometer 110 comprises a pair of opposed electrode plates 112 surrounded by an electrical insulator 114 that supports the electrode plates 112 and insulates them from other conductive elements. The electrode plates 112 surround a drift gas 116 that drifts from an input end or inlet 118 of the differential mobility spectrometer 110 to an outlet or output end 120 of the differential mobility spectrometer 110. Differential mobility spectrometry applies RF voltages, referred to herein as separation voltages (SV), across the electrode plates 112 to generate an electric force in a direction perpendicular to that of the drift gas flow. Ions of a given species tend to migrate radially away from the axis of the drift tube by a characteristic amount during each cycle of the RF waveform due to differences in mobility during the high field and low field portions. A DC CoV, is applied to the electrode plates 112 to provide a counterbalancing electrostatic force to that of the SV.

In accordance with various aspects of the present teachings, a controller 122 can be operably coupled to the differential mobility spectrometer 110 and configured to control the DC and RF voltages applied to the electrodes such that ions having a mass in a selected range from about 200 amu to about 2000 amu (or in a range from about 100 amu to about 2000 amu, or in a range of about 150 amu to about 2000 amu) are preferentially transmitted to the outlet end 120. By way of example, the controller can be configured to modulate the RF and DC potentials applied to the electrodes so as to generate a fringing field in proximity to the input end 118 of the differential mobility spectrometer 110. Applicants have discovered that such a fringing field can be effective, for example, to deflect ions having a mass greater than about 2000 amu (e.g., in a range of about 2000 amu to about 2,000,000 amu) or less than about 200 amu from the axis of the differential mobility spectrometer such that these ions are neutralized (i.e., collide) with the electrodes proximate to the inlet 118. Additionally or alternatively, the controller can control the CoV and SV applied to the electrode plates 112, for example, such that low-mass ions (e.g., ions having a mass less than about 200 amu) are deflected into the electrodes 112 as they are transported through the differential mobility spectrometer 110 while entrained in the drift gas 116. Without being bound by an particular theory, it is believed that low mass ions exhibit increased mobility and/or experience an increased force as they are transmitted through the electric field within the differential mobility spectrometer such that the deflection of these low-mass ions is sufficient such that these ions collide with the electrodes 112. In some aspects, the controller can be configured to operate the differential mobility spectrometer at a resolution of less than about 10, 5, or 1.

The outlet end 120 of the differential mobility spectrometer 110 releases the drift gas 116 and ions transmitted through the differential mobility spectrometer 110 towards an inlet 154 of a vacuum chamber 152 containing the mass spectrometer 150.

The drift time through the flight tube and therefore the mobility of an ion is characteristic of the size and shape of the ion and its interactions with the background gas. As shown in FIG. 2, the differential mobility spectrometer 110 can be contained within a curtain chamber 130 that is defined by a curtain plate or boundary member 132 and is supplied with a curtain gas from a curtain gas supply 134. Specifically, curtain gas from curtain gas supply 134 can flow through curtain gas conduit 136 at flow rates determined by a flow controller and valves. The curtain gas supply 134 can provide any pure or mixed composition curtain gas to the curtain gas chamber. By way of non-limiting example, the curtain gas can be air, $O_2$, He, $N_2$, CO2, or any combination thereof. The pressure of the curtain gases in the curtain chamber 130 can be maintained at or near atmospheric pressure (i.e., 760 Torr). Additionally, the curtain gas can be modified with any type of modifier or mixture of modifiers known in the art for purposes such as clustering, suppressing discharge, limiting proton transfer, chemically modifying ions, forming complexes or bonds or other purposes.

Ions can be provided from an ion source (not shown) and emitted into the curtain chamber 130 via curtain chamber inlet 144. As will be appreciated by a person skilled in the art, the ion source can be virtually any ion source known in the art, including for example, a continuous ion source, a pulsed ion source, an atmospheric pressure chemical ionization (APCI) source, an electrospray ionization (ESI) source, an inductively coupled plasma (ICP) ion source, a matrix-assisted laser desorption/ionization (MALDI) ion source, a glow discharge ion source, an electron impact ion source, a chemical ionization source, or a photoionization ion source, among others. The pressure of the curtain gases in the curtain chamber 130 (e.g., ~760 Torr) can provide both a curtain gas outflow 142 out of curtain gas chamber inlet 144, as well as a curtain gas inflow 137 into the differential mobility spectrometer 110, which inflow 137 becomes the drift gas 116 that carries the ions through the differential mobility spectrometer 110 and into the mass spectrometer 150 contained within the vacuum chamber 152, which can be maintained at a much lower pressure than the curtain chamber 130. For example, the vacuum chamber 152 can be maintained at a pressure of 2.3 Torr by a vacuum pump.

As shown in FIG. 2, the ion mobility system/mass spectrometer system 100 can additionally include a port 124 and a vacuum pump 126 located between the outlet end 120 of the differential mobility spectrometer 110 and an inlet 154 of a vacuum chamber 152, through which gas can be drawn out of the curtain chamber 130. It will be appreciated by a person skilled in the art, that by increasing the rate at which gas is drawn through the port 124, the gas flow rate of the drift gas 116 through the differential mobility spectrometer 110 can be increased, thereby decreasing the transit time of ions travelling therethrough.

Thus, whereas prior art differential mobility spectrometers are configured to optimize selectivity (e.g., by increasing transit time of the drift gas 116 such that the target analyte can be separated from an interfering species at the expense of sensitivity (i.e., through neutralization of the interfering species on the electrodes by tuning the CV to preferentially transmit an ion of interest or by altering the CV such that peaks between various species can be resolved as the CV is ramped), systems in accord with the present teachings exhibit transit times that minimize losses (e.g., maximize transmission, increasing peak width and height) of species exhibiting a broad range of m/z and mobilities.

By way of example, in systems in accord with the present teachings, the drift gas 116 can impart transit times for the ions through the differential mobility spectrometer 110 of less than 7 ms (e.g., 6.5 ms, less than 5 ms, less than 2 ms, less than 1 ms). Though such transit times can result in the differential mobility spectrometer exhibiting a reduced resolution, the drift gas 116 flow rate through the ion mobility spectrometer 110 can ensure that ions of interest transit through the spectrometer with minimal loss, if any, e.g., a loss of less than about 50%, or less than about 20%, or less than about 10%, while the high mass (e.g., greater than 2000 amu) and low mass ions (e.g., less than 200 amu) are filtered out (e.g., deflected off-axis so as to collide with an electrode 112) as discussed otherwise herein.

Moreover, it will be appreciated in light of the present teachings that other variables can be selected so as to maximize transmission through the ion mobility spectrometer. By way of non-limiting example, the dimensions of the differential mobility spectrometer 110, the number gas density, the pressure of the curtain chamber, and/or the flow rate of the drift gas can be modulated so as to optimize transmission. For example, the ion mobility spectrometer can be configured with gas flows and cell dimensions scaled to provide resolutions sufficiently low to provide transmission efficiencies greater than 50% for a broad mass range of interest. By way of non-limiting example, in an ion mobility spectrometer having a length of about 30 mm (1×10×30 mm) along its transmission axis and a distance between electrodes of about 1 mm, a flow rate of about 3.8 L/min can result in a residence time of about 4.2 ms while a flow rate of about 6.5 L/min can result in a residence time of about 1.8 msec.

With reference again to FIG. 2, the mass spectrometer system 100 can be operated so as to set the flow rate of the drift gas 116 with the port 124 closed to about 2.8 L/min, by way of non-limiting example. In various embodiments, the port 124 can be opened and the pump 126 operated such that the flow rate increases to a rate, e.g., greater than about 4 L/min, greater than about 5 L/min, greater than about 6 L/min, or about 7 L/min. It will further be appreciated that the differential mobility spectrometer 110 can also be dimensioned so as to provide a decreased path length (e.g., shorter electrode plates 112) to reduce transit time. Thus, the present teachings enable that the transit time of ions through the differential mobility spectrometer 110 can be selected to optimize transmission of ions of interest through the differential mobility spectrometer 110 into the mass analyzer 150.

As will be appreciated by a person skilled in the art, the mass spectrometer 150 can additionally include mass analyzer elements 150a downstream from vacuum chamber 152. Ions can be transported through vacuum chamber 152 and may be transported through one or more additional differentially pumped vacuum stages containing one or more mass analyzer or ion transport elements 150a. For instance, in one embodiment, a triple quadrupole mass spectrometer may comprise three differentially pumped vacuum stages, including a first stage maintained at a pressure of approximately 2.3 Torr, a second stage maintained at a pressure of approximately 6 mTorr, and a third stage maintained at a pressure of approximately $10^{-5}$ Torr. The third vacuum stage can contain a detector, as well as two quadrupole mass analyzers with a collision cell located between them. It will be apparent to those skilled in the art that there may be a number of other ion optical elements in the system. Other type of mass analyzer such as single quadrupole, ion trap (3D or 2D), hybrid analyzer (quadrupole-time of flight, quadrupole-linear ion trap, quadrupole-orbitrap), orbitrap or time-of-flight, could also be used.

In operation, a sample containing or suspected of containing an analyte(s) of interest can be prepared in accordance with various methods as known in the art for introduction into the differential mobility spectrometer 110. The ions can be generated adjacent the inlet 150 of the curtain chamber 130 and then transported through the differential mobility spectrometer 110 that is configured to remove both low-mass ions (e.g., ionized solvent molecules exhibiting less than 200 m/z or less than 100 m/z) and high-mass ions (e.g., charged residues exhibiting greater than 2000 m/z or a mass greater than 2000 amu). The remainder of ions (e.g., ions exhibiting m/z in a range of about 200 Da to about 2000 Da) can be transmitted by the differential mobility spectrometer 110 to downstream mass analyzer elements 150, 150a for further analysis or detection, as is known in the art.

As indicated above, contamination of mass spectrometer ion paths by substances created during the electrospray ionization of samples and solvents is of major concern. Costly and time consuming cleaning procedures are required to ameliorate the problem. Extensive efforts have been employed to develop devices to minimize or eliminate this problem. To date, the field has focused on the use of shadow stops or curvatures in ion guides located in the vacuum system of the mass spectrometer to filter neutral components thought to be the cause of contamination from the ion beam. Neutral particles follow a straight trajectory through curved fields whereas ions and charged particles follow the fields. If neutral particles were the primary source of contamination, then curved ion guides or shadow stops would eliminate them and prevent them from going deeper into the vacuum system where they can do more damage. If, however, the main source of contamination was charged particles and high ion currents from electrospray solvents, this approach would serve no purpose because the charged contaminants would follow the curved fields and travel around any shadow stops.

Furthermore, the present teachings are based on the discovery that a high transmission, low resolution ion mobility device can filter the high mass ions or charged debris to keep the vacuum system of a mass spectrometer clean for long periods of time. The device configuration takes into account the residence time of the ions through the ion mobility spectrometer, the gap height between the electrodes of the ion mobility spectrometer, and the maximum separation voltage applied to the ion mobility spectrometer, wherein a ratio of the residence time of the ions through the ion mobility spectrometer to the product of gap height between electrodes of the ion mobility spectrometer and the maximum separation voltage being less than 0.002. In various aspects, a ratio of the residence time of the ions through the ion mobility spectrometer to the product of gap height between the electrodes of the ion mobility spectrometer and the maximum separation voltage applied to the electrodes of the ion mobility spectrometer being less than 0.0015. Conventional prior art ion mobility devices have been configured to achieve high selectivity to maximize the separation power at the expense of transmission of the ions and sensitivity differing from the Applicants' counter-intuitive teachings of a low resolution ion mobility device designed to filter charged particles prior to the vacuum system while achieving high transmission of ions.

In various aspects, the residence time of the ions can be less than 100 ms. In various aspects, the gap height can be between 0.02 and 5 millimeters. In various aspects, the SV comprises an RF signal applied to the electrodes, and including a CoV comprised of a DC signal applied to the electrodes, and wherein the RF and DC signals are configured to generate a fringing field in proximity of said input end of the ion mobility spectrometer effective to cause said ions having a selected mass to follow off-axis trajectories to collide with said electrodes in proximity to said input end. In various aspects, the method and system further comprise selecting a transit time of the ions through the ion mobility spectrometer to facilitate transit of analytes of interest through the ion mobility spectrometer. In various aspects, the transit time can be selected to provide transmission efficiency of greater than 50% for a broad mass range of ions. In various aspects, the ion mobility spectrometer comprises a differential mobility spectrometer or a FAIMS system.

Figure 5:
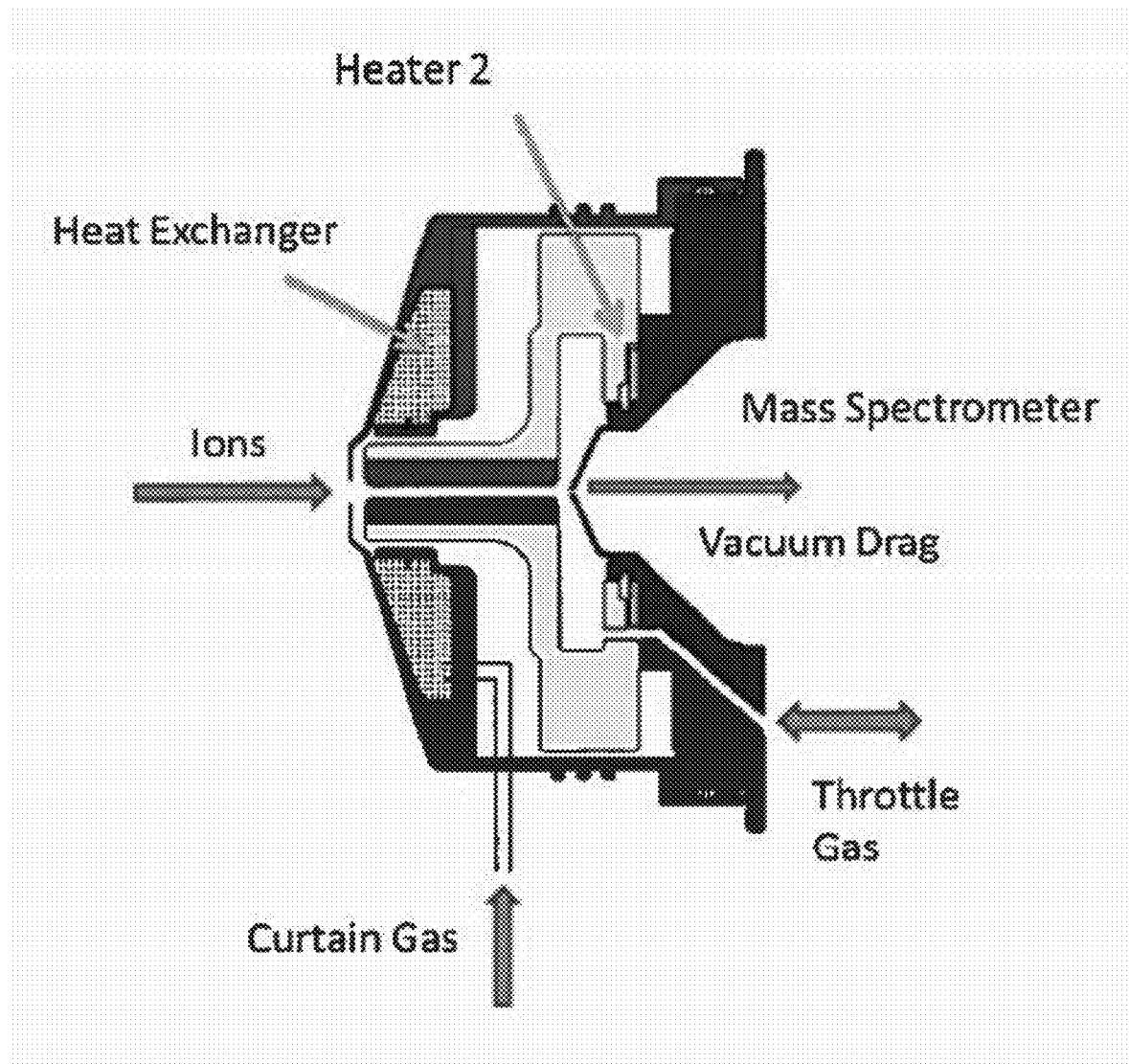
FIG. 5 shows an example of a commercial DMS coupled to a mass spectrometer in accordance with the applicants' teachings.
Figure 6A:
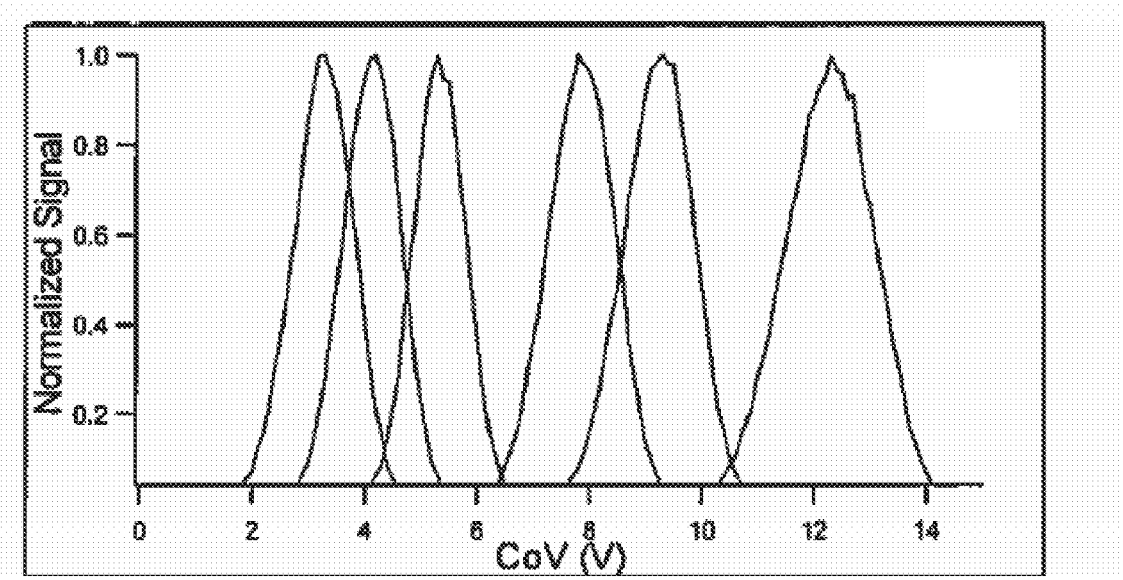
FIGS. 6A and 6B show ionograms illustrating the effect of residence time on resolution in a DMS coupled to a mass spectrometer in accordance with the applicants' teachings.
Figure 6B:
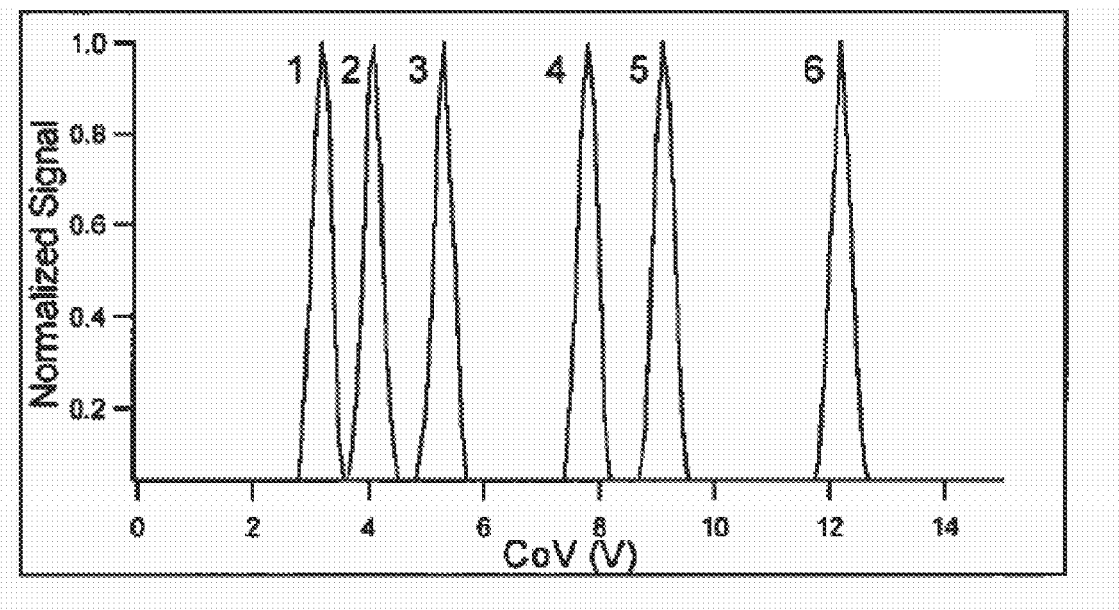
Figure 7A:
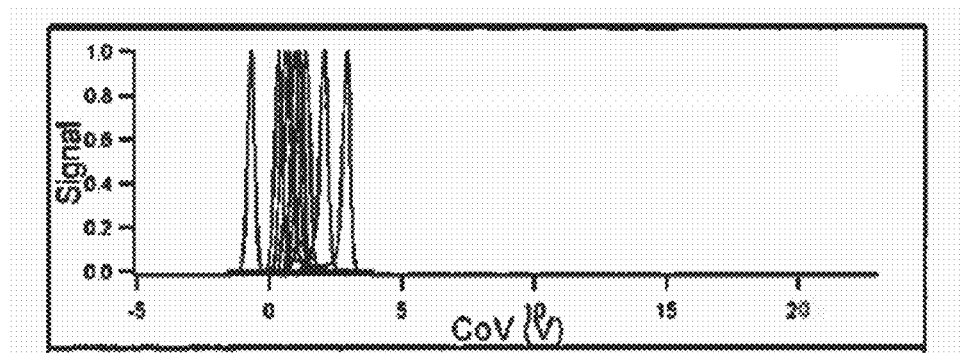
FIGS. 7A-7D show ionograms illustrating the changes in the peak capacity of a DMS device resulting from altering gap height in accordance with the applicants' teachings.
Figure 7B:
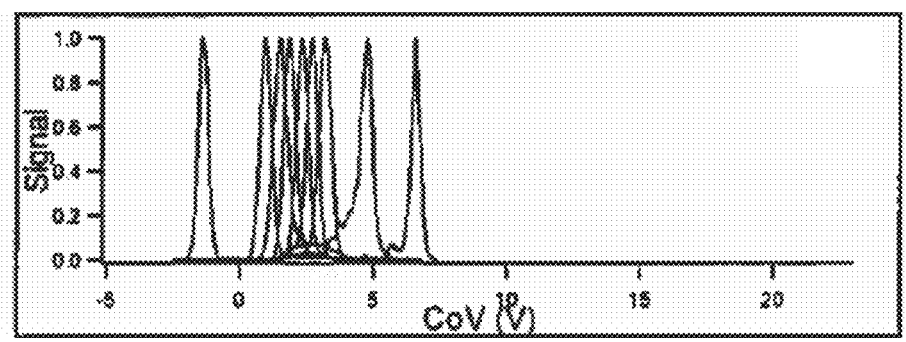
Figure 7C:
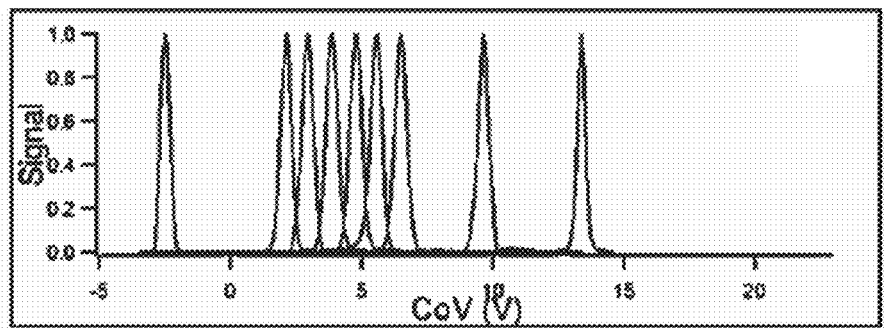
Figure 7D:
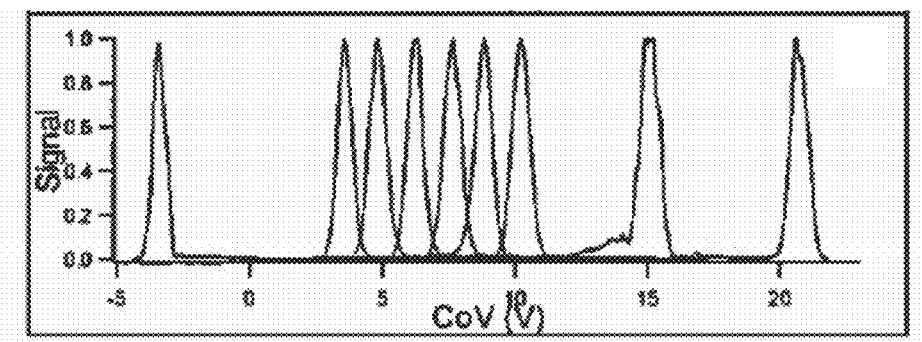
Figure 8:
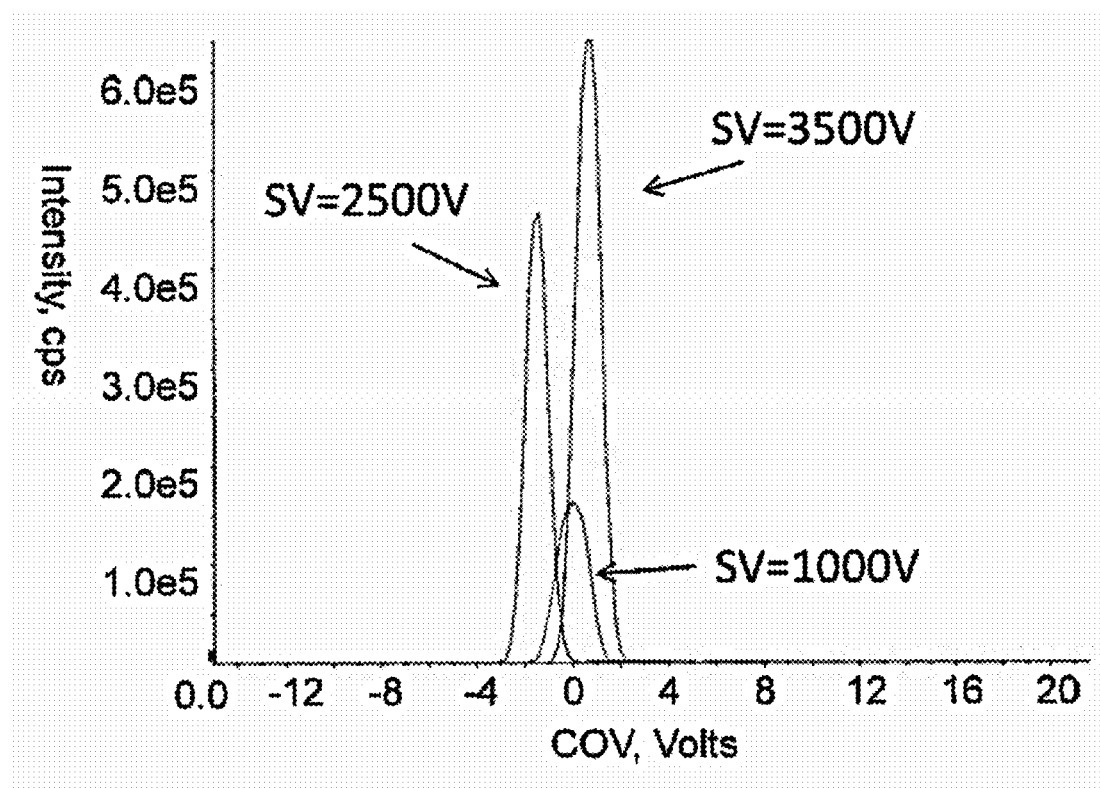
FIG. 8 shows ionograms of methylhistamine at different separation voltages demonstrating an increase in ion transmission with increasing separation voltage in accordance with the applicants' teachings.
Figure 9A:
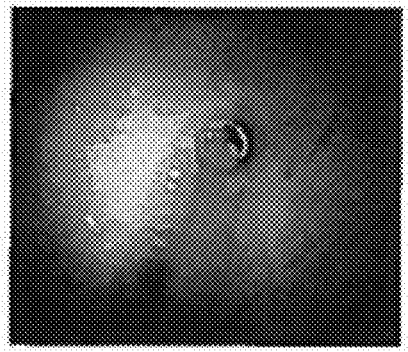
FIGS. 9A-9C show contamination from charged debris in accordance with the applicants' teachings.
Figure 9B:
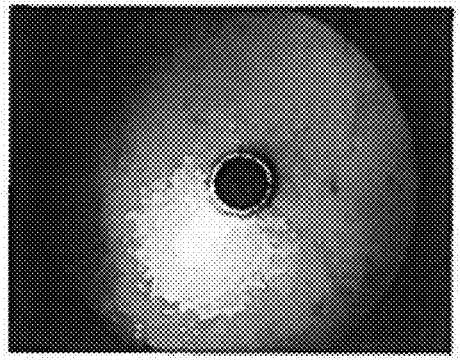
Figure 9C:
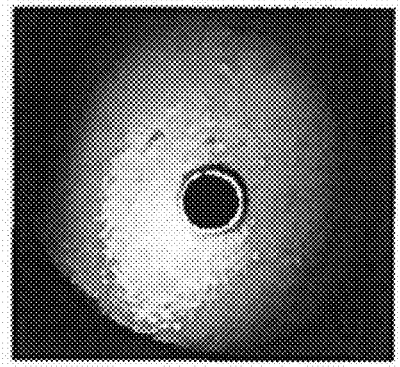

Experiments were conducted to determine whether the main source of mass spectrometer contamination was from neutral particles or charged substances, the results are shown in FIGS. 9A-9C. The experiments were done on a commercial electrospray mass spectrometer with an atmospheric interface depicted in FIG. 5 with the DMS cell both installed and removed. The interface comes equipped with a counter current flow of gas, the purpose of which is to blow neutral particles away from the atmospheric entrance aperture while ions and charged particles follow the electric fields and travel against the curtain gas flow. An accelerated contamination test was developed using a common commercial biological buffer solution referred to as Hank's buffer. The aqueous Hank's buffer solution was infused under normal operating conditions with the high voltage applied to the pneumatically nebulized electrospray emitter to charge the droplets with the curtain gas on at all times at sufficient velocity to eliminate neutrals. As shown in FIG. 9A, after 15 hours the atmospheric aperture was clogged with material from the sample when the ion source was operated in the normal way, with the sprayer voltage on. For the material to have penetrated the curtain gas, it had to be charged.

The experiment was repeated with all conditions identical except a DMS cell according to the Applicants' teachings was installed. As seen in FIG. 9B, after 24 hours the atmospheric aperture was free of any visible contamination. All of the charged debris was deflected at the entrance of the cell and most importantly before entering the vacuum system of the mass spectrometer where the serious damage can occur. As in the first case, the curtain gas was on at sufficient levels to eliminate neutral materials.

To make sure the curtain gas was deflecting neutral materials that could be generated by the spraying of Hank's buffer, a third experiment was done with the results shown in FIG. 9C. The DMS cell was removed, and the same sample run this time spraying only by means of the pneumatic nebulizer; the high voltage to the electrospray emitter was off. Under this condition, no charging of the sample is occurring but abundant neutral droplets and uncharged particles are created. No build up of debris was observed on the atmospheric aperture proving that the curtain gas was effectively eliminating all neutral materials, and the source of the mass analyzer contamination was from charged particles and ions.

Photographs of critical lens elements from the mass spectrometer inlet and inside the vacuum further corroborating the effectiveness of the DMS as a charged debris filter according to the Applicants' teachings are shown in FIGS. 10A-10B. Critical lenses inside the vacuum system were observed to be contaminated after the experiment in FIG. 9A as shown in FIG. 10A and free of any debris under conditions in FIG. 9B as shown in FIG. 10B.

Charged materials generated by an electrospray process can take two forms. It can be in the form of charged molecules (ions); the vast majority of which is the electrospray solvent. The overwhelming abundance and intensity of the ion current from the solvent ions can be readily seen in a mass spectrum. It may be possible that they can be a source of ion burn on critical lenses inside the vacuum system. But, solvent ions are volatile and cannot be expected to build up debris to the extent as that shown in FIG. 9A where the vacuum system was nearly plugged off. The charged debris that accumulated can also be coming from the dissolved substances in the sample.

Subsequent to this experiment, the inventors have discovered the existence of previously unknown physical entities in the form of substances with very high mass to charge ratio beyond the mass range of mass spectrometers. We have characterized their nature with a novel scan mode for a tandem mass spectrometer that we developed specifically for this purpose. These substances are ubiquitous and an inherited by-product of electrospray ionization. All indications are that they are a major source of mass spectrometer analyzer contamination. It is these substances, in combination with the extremely high ion currents that are produced by electrospray from the low mass solvent ions, which can cause the fouling of critical components in the ion path located in the vacuum system of mass spectrometers leading to distortions in the electric fields of the mass filters and focusing lenses resulting in reduced performance. An understanding of these substances and their effect on analyzer contamination is neither known nor obvious in the current state of the science involving mass spectrometry.

The scan mode we developed to prove the existence of these high mass charged particles is described below and is referred to as the "Asteroid scan." It has no analytical purpose other than as a means to observe and quantitate these materials. The Asteroid scan can be done on a triple quadrupole mass spectrometer. All samples will produce asteroids, but the more organic and inorganic solutes in the electrospray solvent, the more asteroids are produced. The asteroids can be tracked by adding to the solvent a standard reference compound such as reserpine which becomes trapped in the asteroid during the ionization process. The sample is infused into the ion source. Quadrupole 1 mass filter is set to open resolution at m/z 1250 by dropping the mass resolving DC voltage ramp. Under these conditions, no ions below m/z 1000 pass Q1, but all ions and charged particles above m/z 1000 pass. Collision gas is put into the collision cell, and the collision energy is initially set to 0 volts. When quadrupole 3 is scanned, the resulting mass spectrum shows no ions at any mass. As the collision energy is raised to 150 eV, ions from the seed compound begin to appear in the Q3 spectrum and increase in intensity as they are released from the high mass charged particle.

FIGS. 1(A)-1(C) provide an example. FIG. 1(A) is a standard product ion scan of reserpine to use as a reference for identifying the molecular ion and fragment ions from reserpine during subsequent asteroid scans. Reserpine typically fragments at 47 eV collision energy. When the collision energy is set to 0 during the asteroid scan, no ions, including the molecular ion at m/z 609, can be observed. As seen in FIG. 1(B), at 50 eV, the molecular ion from reserpine at m/z 609 is released from the asteroid and appears in the Q3 spectrum. It is not fragmenting as it did in the conventional product ion scan at 47 eV because much of the vibrational energy is absorbed by the other components of the high mass charged particle. In FIG. 1(C), at 100 eV, the product ion fragments of reserpine are observed along with many other unidentified ions. The unidentified ions are coming from other unknown components of the asteroid or charged particle.

FIG. 11 shows that the amount of material captured in the asteroids can be significant and that they are filtered by the DMS fields according to the Applicants' teachings. In this case, Q3 is set to monitor only the ions from reserpine and no others. At 5 eV collision energy, virtually no signal is observed, and at 70 eV several orders of magnitude signal rise is seen. The DMS cell is installed but both SV and CoV are off so no filtering is occurring. When the CoV is turned on to 100V, the asteroids are removed and return when the voltage is turned back off. When the SV is set to 4000V, a similar filtering action is observed. This data validates the photographic observations in FIGS. 9A-9C and 10A-10B.

The understanding of the existence of these high mass charged particles and their role in analyzer contamination is new knowledge. It presents the opportunity for a new application of a DMS based device that would require design characteristics substantially different from the current status that teaches away from optimizing the performance specifications of current generation DMS mobility cells. The ideal contamination filter would first remove charged particles before entering the vacuum system which is essentially what current DMS cells do. But, it would also have broad band pass characteristics which would limit its separation capability to only the removal of high mass charged particles and low mass solvent ions. This would mean the design would drive toward very low resolution and peak capacity instead of high resolution and peak capacity. The separation of isobars would no longer be of any relevance to the design of this device given its primary application of the maximization of ion transmission whereas in the prior art, this figure of merit was secondary to resolution and peak capacity.

In order to achieve the goal of maximum ion transmission efficiency while maintaining adequate resolution and peak capacity to serve as a broad band pass contamination filter, the relationship of three key design elements are considered. These elements are ion flight time, cell gap height, and maximum separation voltage. Following is data describing the effect that each one has on the three performance characteristics for the basic DMS described in FIG. 5. The relative trends that these figures of merit exhibit will be generalizable to any particular design and thus are not limited to any particular design. In addition the design specifications for the currently described commercial and noncommercial DMS and FAIMS analyzers will be described and compared to the optimized values we propose for an ideal contamination filter.

Figure 3:
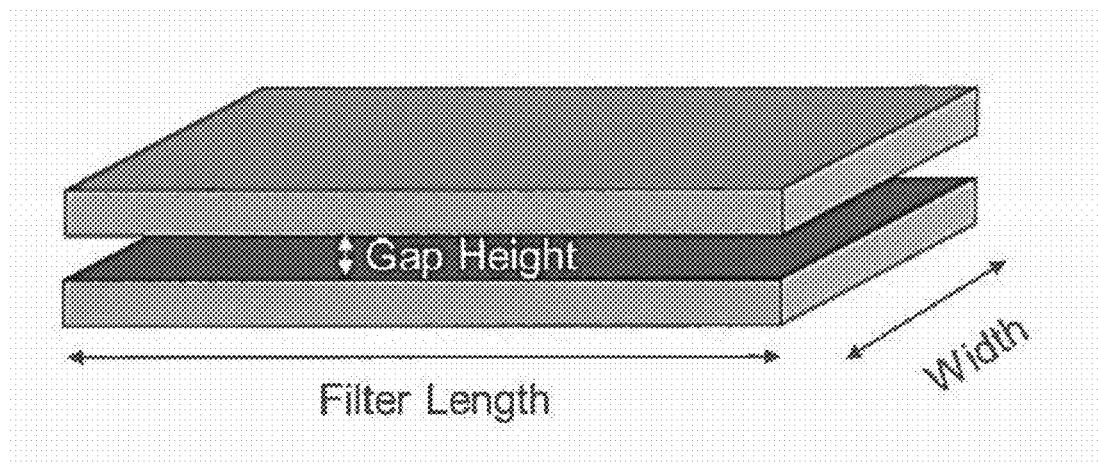
FIG. 3 shows a schematic of a rectangular, planar DMS sensor in accordance with various aspects of the applicant's teachings.
Figure 4A:
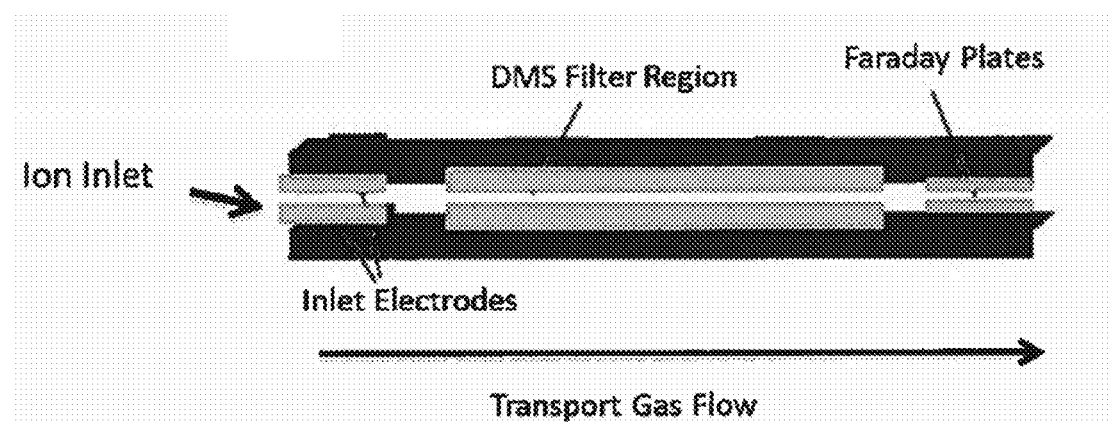
FIG. 4A shows a schematic of a stand-alone DMS sensor in accordance with various aspects of the applicants' teachings.
Figure 4B:
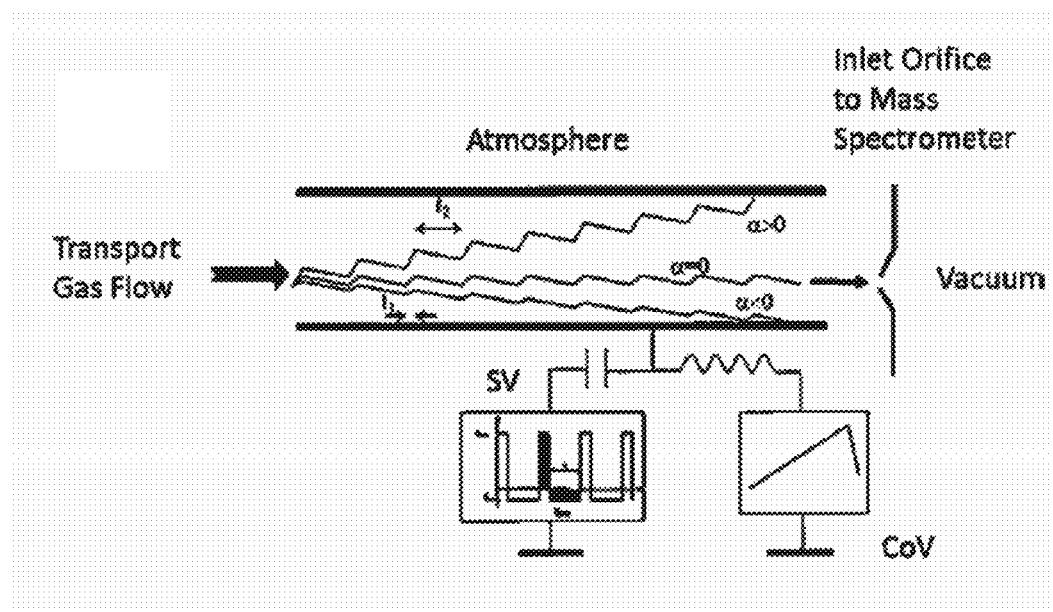
FIG. 4B shows a schematic of a DMS with a mass spectrometer as the ion detector and depiction of the asymmetric waveform in accordance with the applicant's teachings.
Figure 12:
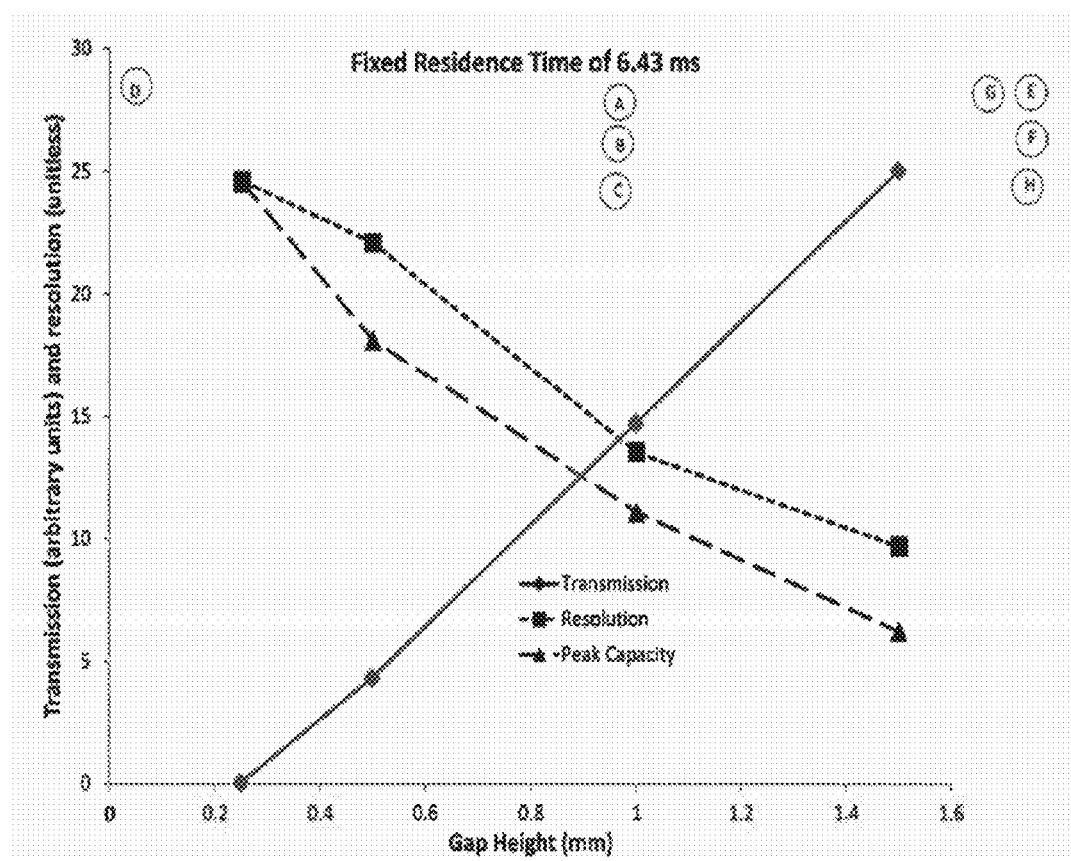
FIG. 12 shows the effect of gap height between the DMS electrodes on transmission, resolution, and peak capacity, in accordance with the applicants' teachings.

Gap height is considered in FIG. 12. Ion transmission trends in the opposite direction of resolution and peak capacity for a fixed residence time. From the graph, it would appear that an ideal contamination filter would have the largest gap height possible to maximize transmission, all other elements being equivalent as was done to generate the performance data for this particular cell described with reference to FIGS. 3 and 5. However, as elaborated earlier, optimization of each performance characteristic requires a balancing of several important design elements. Superimposed on the graph in circles are the gap heights of the various commercial and non-commercial DMS and FAIMS devices that have been described in the general literature, as well as two versions of cells optimized as contamination filters. The performance trends on the y-axis generally apply to all but their position on the x-axis varies for each individual system as the gap height is changed. Gap heights can span a large range with very little distinguishing the current generation high resolution devices from the proposed contamination filters. A=Contamination filter 1. B=Contamination filter 2. C=Commercial DMS-MS system. D. Commercial micro machined DMS-MS system. E. Commercial cylindrical FAIMS-MS system. F. Non-commercial DMS-MS system. G. Non-commercial DMS-MS system. H. Commercial cylindrical FAIMS-MS system.

Figure 13:
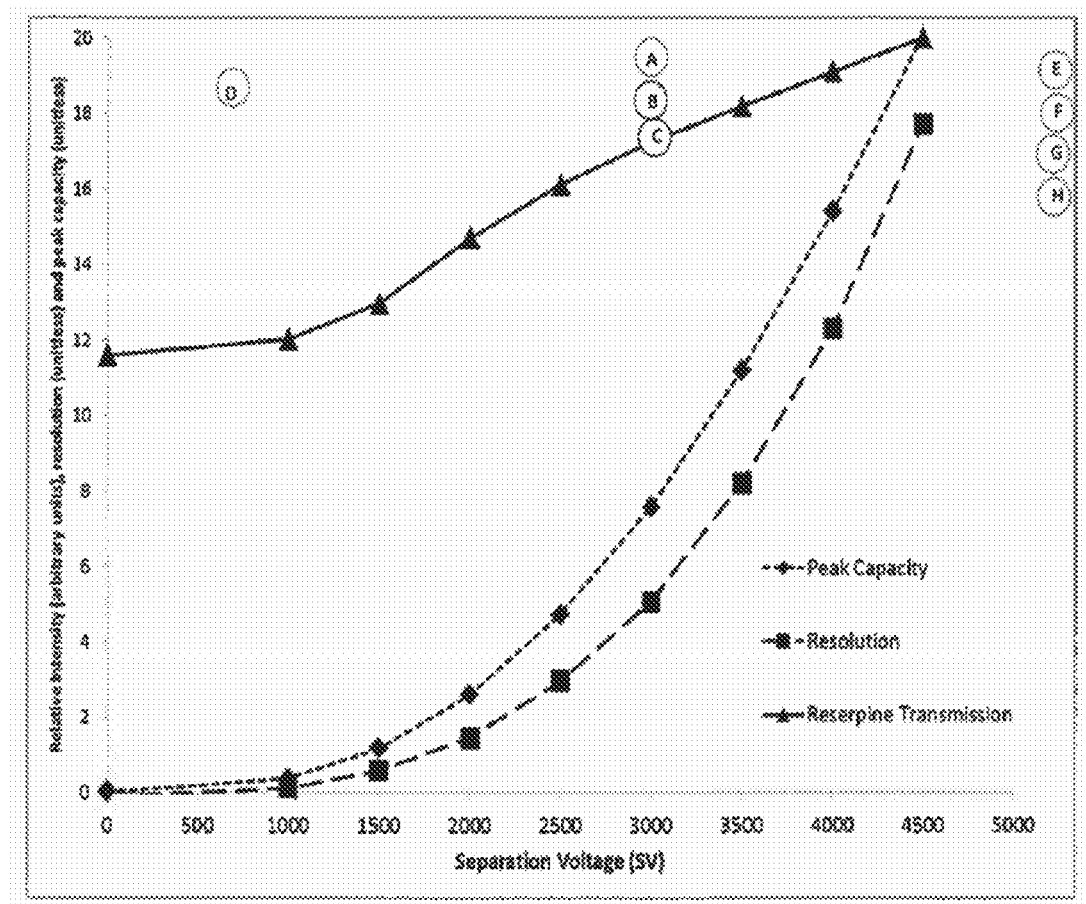
FIG. 13 shows the effect of separation voltage applied to the DMS electrodes on transmission, resolution, and peak capacity, in accordance with the applicants' teachings.

Separation voltage (SV) is considered in FIG. 13. Ion transmission, resolution and peak capacity track together. From the graph, it would appear that an ideal contamination filter could not be designed as high transmission would bring with it high resolution and peak capacity which is not desirable for a broad band pass device. The balancing of the other two design elements can counter this effect. Superimposed on the graph in circles are the separation voltages of the various commercial and non-commercial DMS and FAIMS devices as well as two versions of cells optimized as contamination filters. The performance trends on the y-axis generally apply to all but their position on the x-axis varies for each individual system as the SV is changed. Separation voltage values can span a large range with very little distinguishing the current generation high resolution devises from the proposed contamination filters. A=Contamination filter 1. B=Contamination filter 2. C=Commercial DMS-MS system. D. Commercial micromachined DMS-MS system. E. Commercial cylindrical FAIMS-MS system. F. Non-commercial DMS-MS system. G. Non-commercial DMS-MS system. H. Commercial cylindrical FAIMS-MS system.

Figure 14:
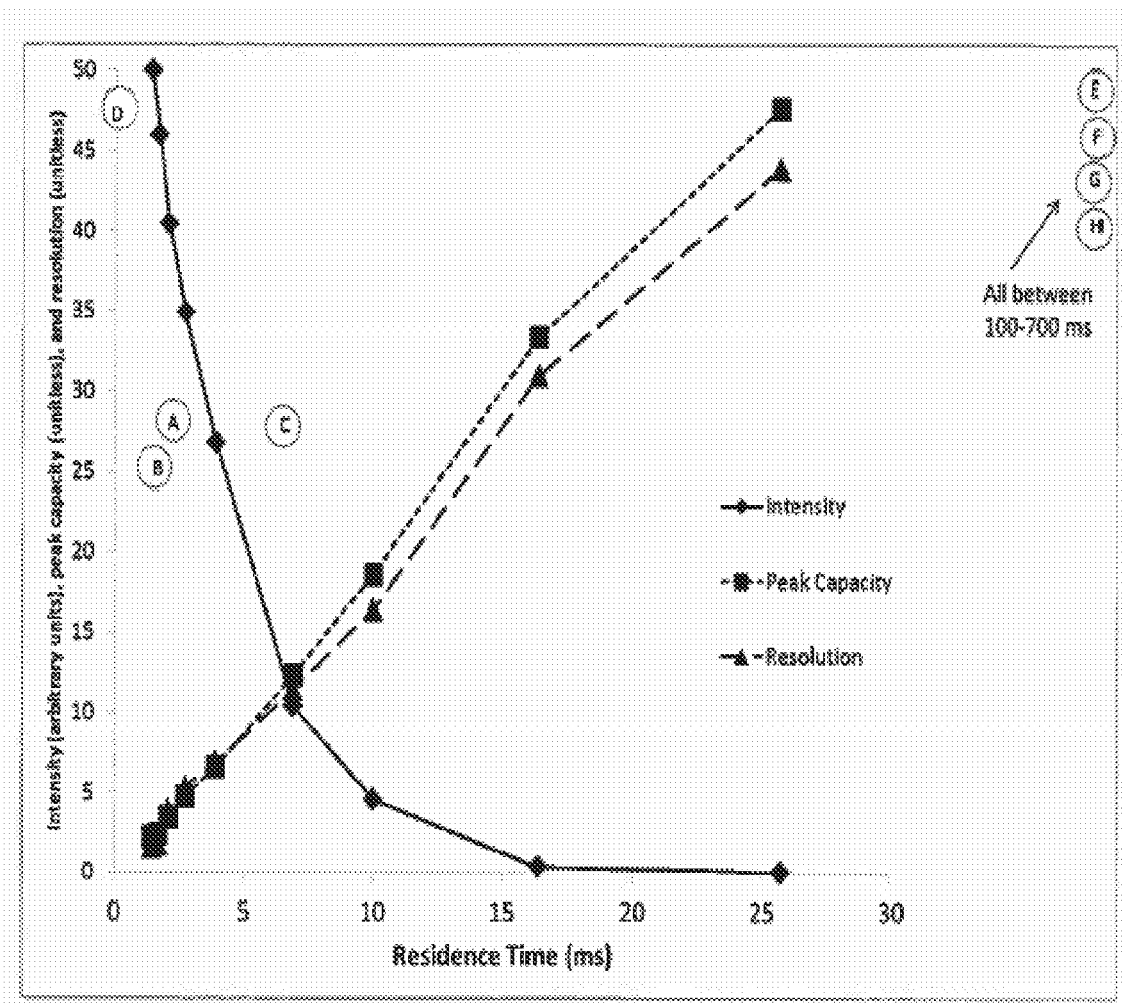
FIG. 14 shows the effect of residence time of ions in the DMS on transmission, resolution, and peak capacity, in accordance with the applicants' teachings.

Flight time also known as residence time is considered in FIG. 14. Ion transmission trends strongly in the opposite direction of resolution and peak capacity. In addition, as the residence time of the ions increases, ion losses become more prevalent, as shown with the diamonds labeled Intensity. From the graph, it would appear that an ideal contamination filter would have the shortest possible flight time to maximize transmission and reduce resolution and peak capacity, all other elements being equivalent as was done to generate the performance data for this particular cell described with reference to FIGS. 3 and 5. Once again, the balancing of the other design elements provides flexibility, and the scatter between the various commercial and non-commercial DMS devices shows no distinguishing cut-off across the boards from versions of cells optimized as contamination filters. The performance trends on the y-axis generally apply to all but their position on the x-axis varies for each individual system as the flight time is changed. However, those shown with the very long flight times have the opportunity to provide the greatest resolution provided the other design parameters are well optimized. A=Contamination filter 1. B=Contamination filter 2. C=Commercial DMS-MS system. D. Commercial micromachined DMS-MS system. E. Commercial cylindrical FAIMS-MS system. F. Non-commercial DMS-MS system. G. Non-commercial DMS-MS system. H. Commercial cylindrical FAIMS-MS system.

The three most important design elements determining the performance characteristics of resolution, peak capacity and transmission are flight time, gap height, and separation voltage. They operate together in a partial inverse relationship we refer to as the Resolution-Transmission Index or RT Index mathematically expressed as:

$$RT = \tau / hSv \qquad \text{(Equation 5)}$$

where $\tau$ is the flight time, h is the gap height, and Sv is the separation voltage.

Figure 15:
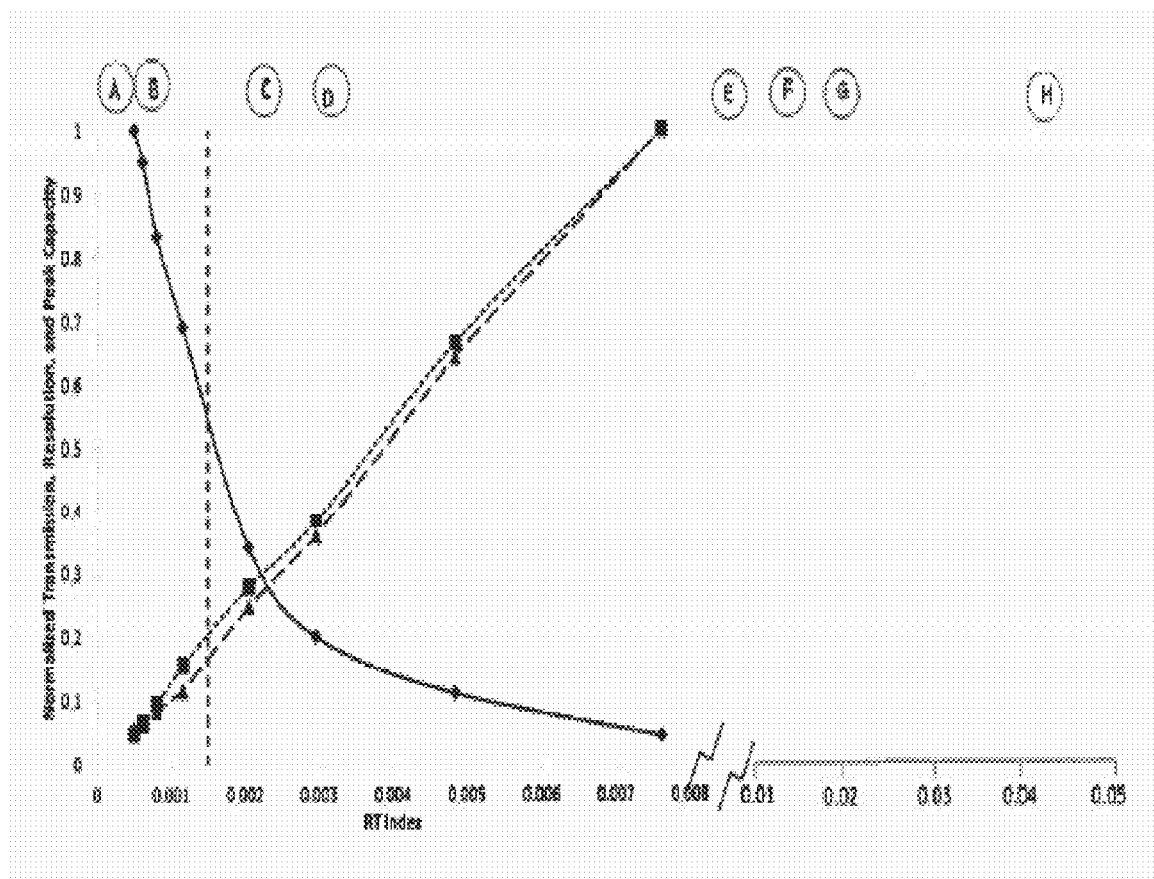
FIG. 15 shows the effect of RT Index on transmission, resolution, and peak capacity in accordance with the applicants' teachings.

RT Index is considered in FIG. 15. When these design elements are considered together in this relationship, and not individually as in the previous three graphs, the plot of the three performance traits can be made on a universal scale applicable to all variations of DMS systems because their interdependence is accounted for in the equation. For all combinations of these design elements, the relative performance graphs apply allowing each to be compared to the other with respect to their performance potentials. At one extreme, the E-H group combines the three design elements to achieve the highest possible resolution their devices can deliver at a severe loss of transmission showing RT indexes that are very large. Notice the non-linearity of the x-axis with the break at an RT value of 0.01. At the other extreme, the contamination filters deliver the maximum ion transmission efficiency their devices can deliver at a cost of resolution and peak capacity which is designed to be sufficient to filter charged debris and low mass solvent ions. In the middle, are analytical devices that try to reach a reasonable compromise to serve as general selectivity enhancement elements for mass spectrometry coupling. The contamination filters reside in a region of the RT index distinct and unique and never exploited before largely due to a lack of appreciation of the potential for this application and a lack of knowledge in the scientific community regarding the particular substances that required filtering, specifically charged high mass particles in addition to low mass solvent ions. This region of design parameters is bounded by a maximum value of RT=0.002 defining a threshold that has hereto for not been breached because of a lack of understanding of its utility and the non-obviousness of its application.

Figure 10A:
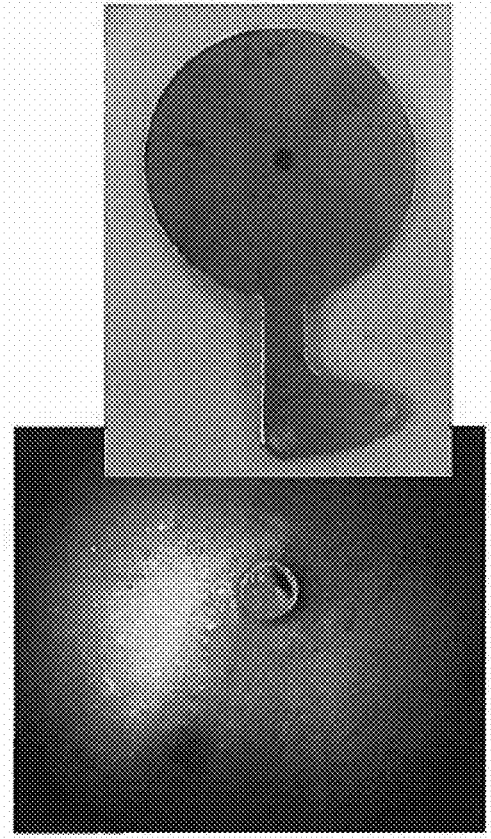
FIGS. 10A-10B show the inlet orifice from a mass spectrometer and lens elements inside the vacuum in accordance with the applicants' teachings.
Figure 10B:
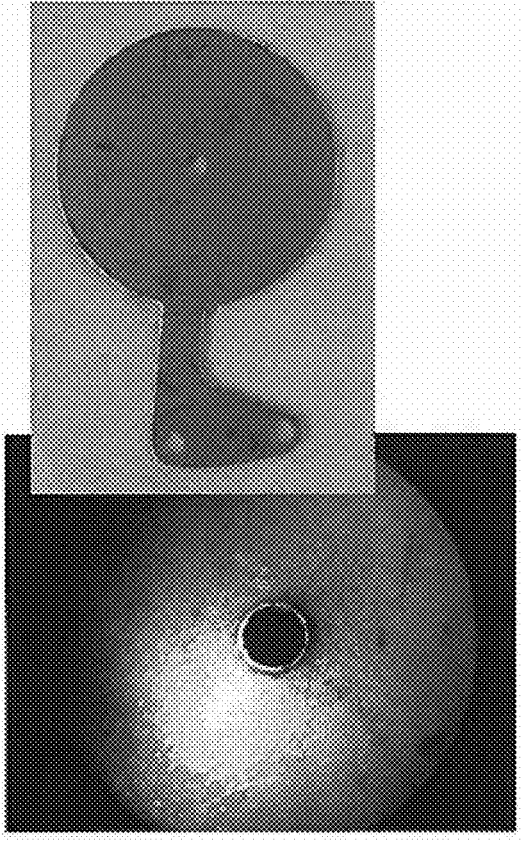
Figure 11:
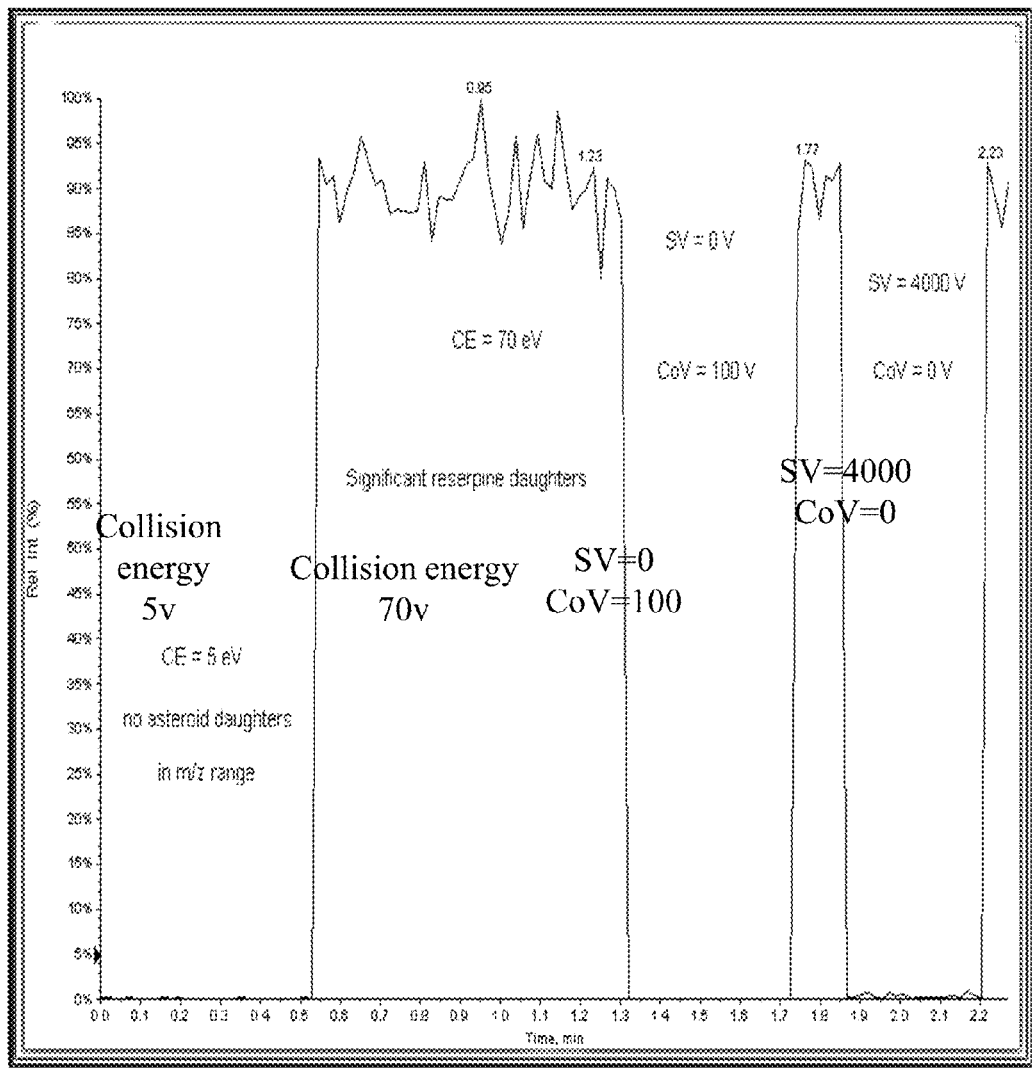
FIG. 11 shows the filtering of debris material by the DMS fields in accordance with the applicants' teachings.
Figure 16A:
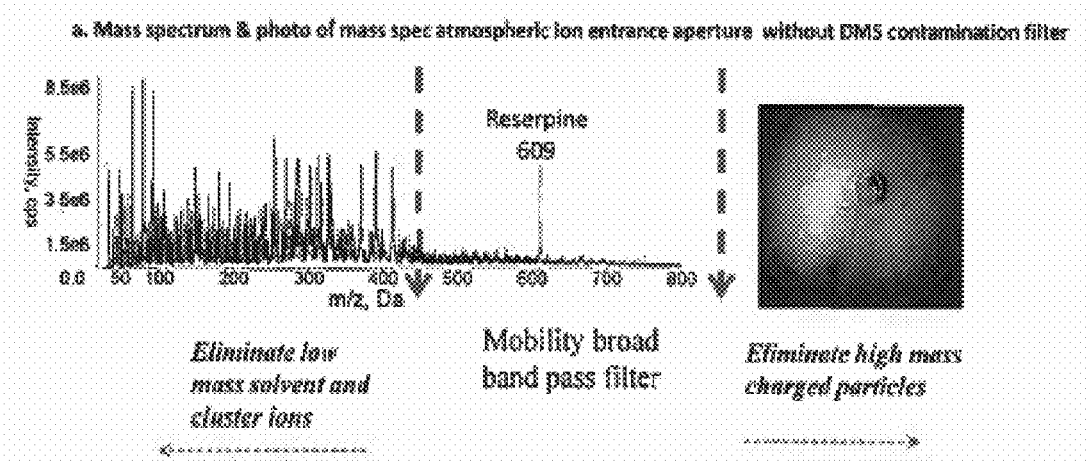
FIGS. 16A-16B show elimination of contamination by the filter in accordance with the applicants' teachings.
Figure 16B:
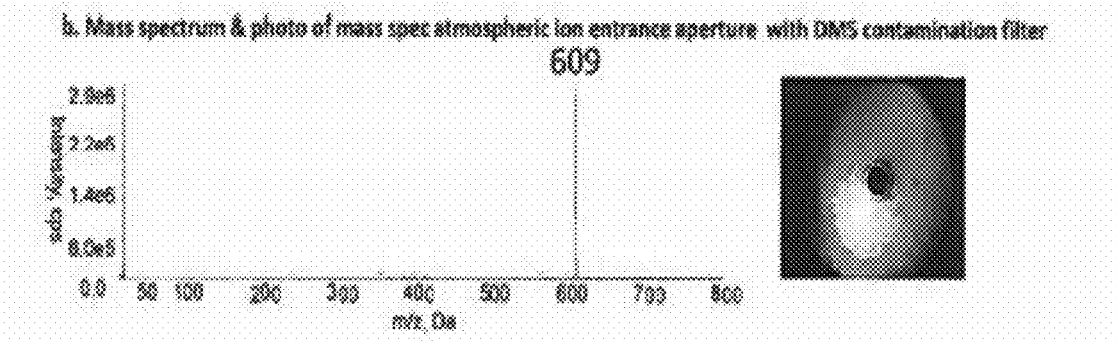
Figure 17:
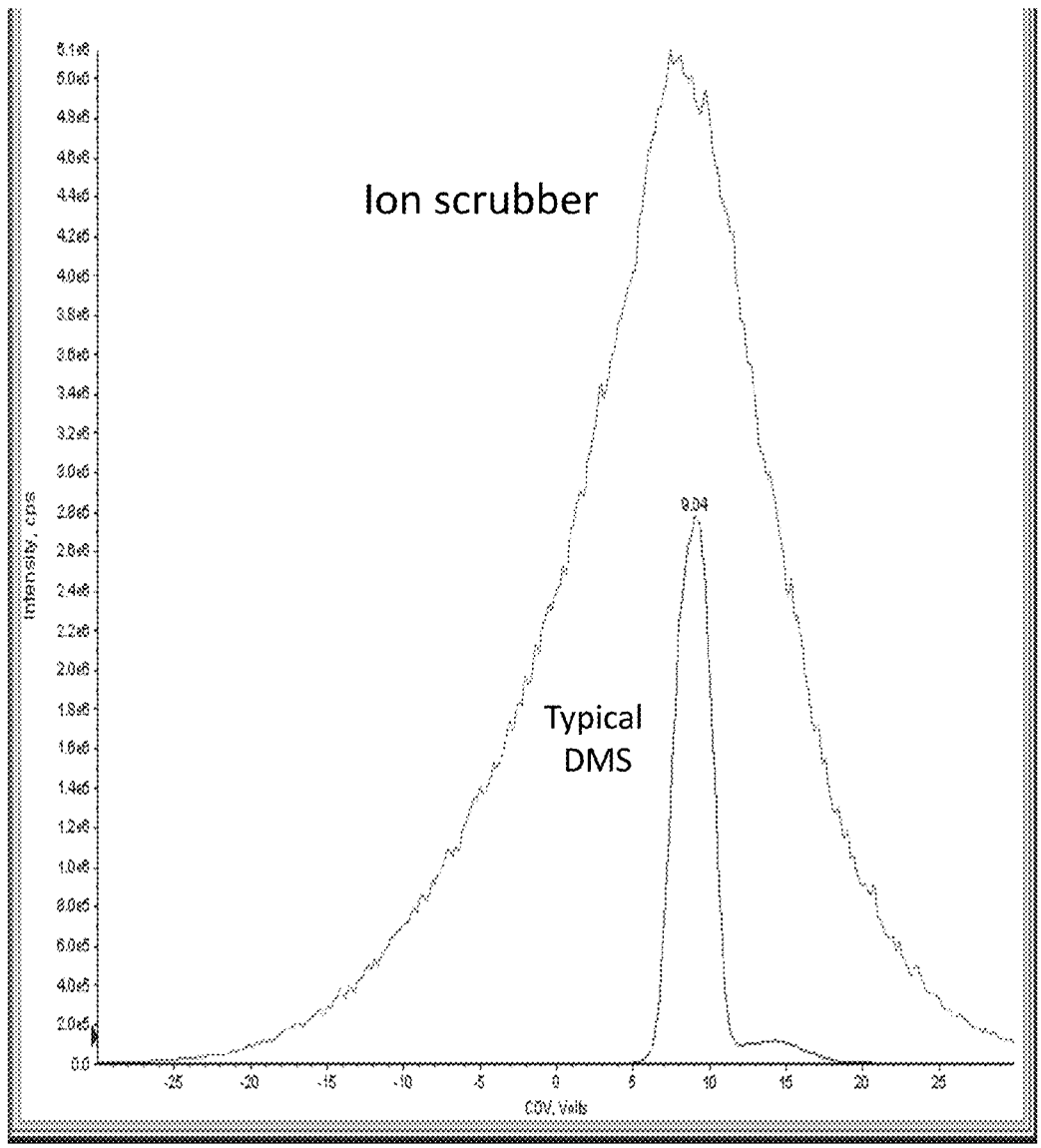
FIG. 17 shows a comparison of the contamination filter and a high resolution DMS in accordance with the applicants' teachings.

The value of a low resolution device is that it allows a large range of analyte ions with a broad range of mobilities to pass without having to alter the SV or CoV voltages. This helps keep the duty cycle of the system to a maximum. FIGS. 16A and 16B demonstrate this principle and also highlight the extent to which unwanted low mass ion current can be eliminated. Although it is not likely that this low mass solvent dominated ion current contributes to the occlusion of the vacuum entrance seen on the right of FIG. 16A and in FIG. 9A because it is inherently volatile, it's great intensity can lead to ion burns on critical focusing elements inside the vacuum system as shown in FIG. 10A. The massive charged particles are responsible for the occlusion and are eliminated as shown in the photographs in FIGS. 9B and 10B. Although uniquely designed to pass broad bands of mobility space, the contamination filter does provide control over the position of this window by adjusting the SV and CoV if fine tuning the filter is required for specific applications. Because it is a mobility filter, it does not bound precise m/z ranges and apriory knowledge of the mobility of the targeted analytes is not generally required because the resolution is so low. The broad band pass nature of the contamination filter compared to a high resolution DMS device can also be appreciated from the ionograms in FIG. 17, where the term ion scrubber is used to describe the high transmission mobility filter according to the Applicants' teachings.

The spectra and images in FIGS. 16A-16B show that the degree to which the filter is eliminating contamination represents several orders of magnitude improvement over not using the device. In principle, this could extend the lifetime of mass spectrometers between costly and time consuming cleaning and repair from a few months to several years.

Figure 18A:
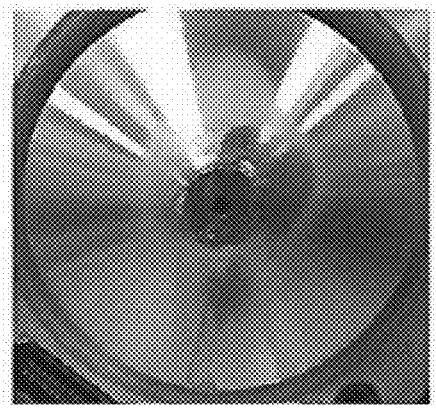
FIGS. 18A-18D show contamination being kept out of the vacuum system and the ion entrance aperture of the mass spectrometer in accordance with the applicants' teachings.
Figure 18B:
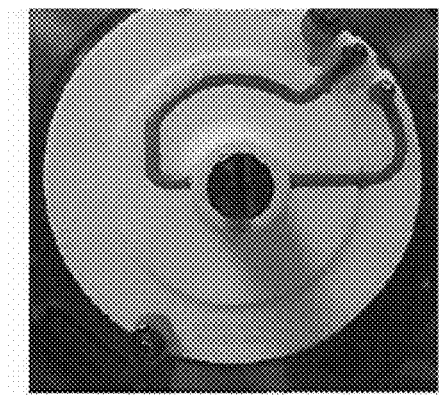
Figure 18C:
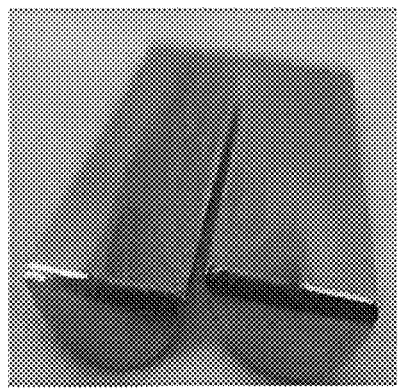
Figure 18D:
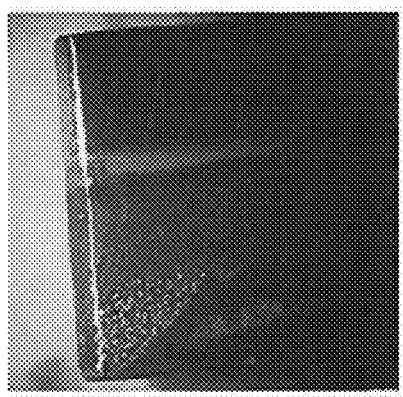
Figure 19:
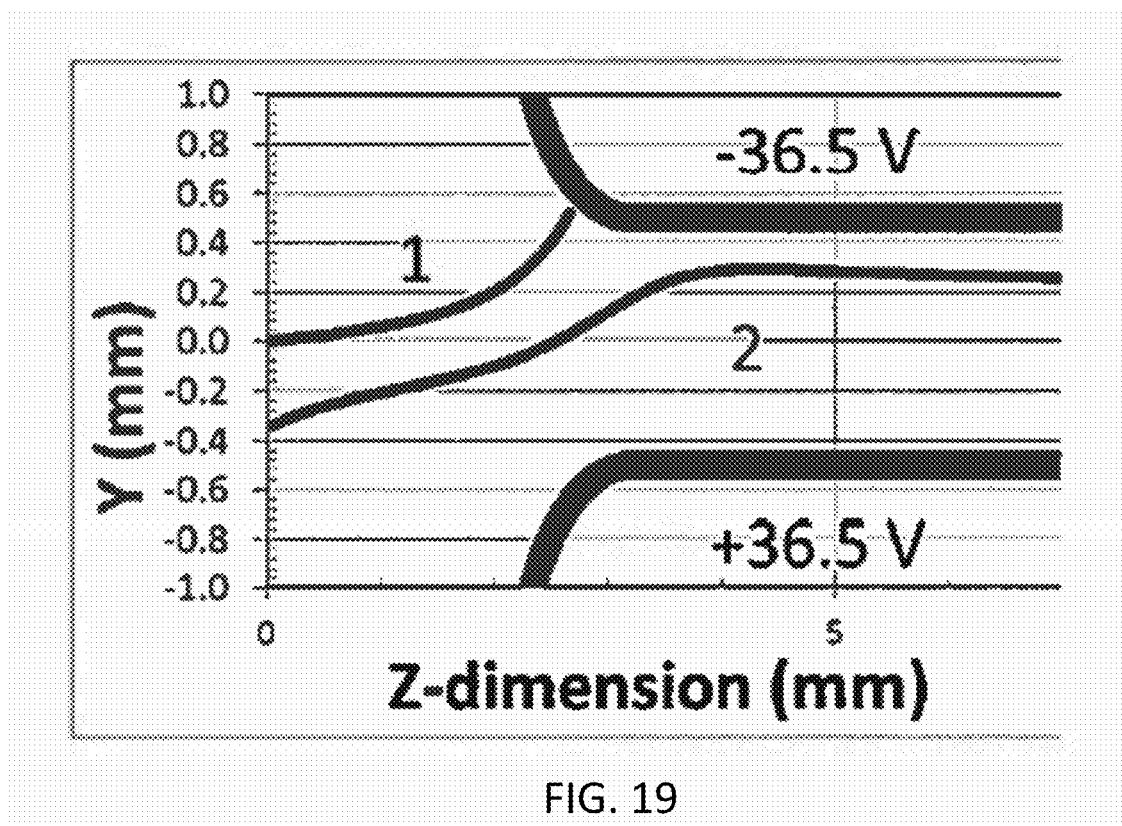
FIG. 19 shows simulations of ions and charged particle trajectories in the entrance region of the DMS cell in accordance with the applicants' teachings.

In accordance with the Applicants' teachings, the majority of contaminating species are being kept out of the vacuum system and away from the ion entrance aperture of the mass spectrometer due to the Applicants' high transmission mobility filter ion scrubber. FIGS. 18A-18D show where the contamination is going. Some material is deposited on the outside of the atmospheric curtain plate as would normally be expected and happens whether or not the filter is installed as shown in FIG. 18A. It produces no detrimental effect on the mass spectrometer when deposited in this region. But a large amount of debris material can be observed on the entrance to the planar DMS cell which visually appears end on as a slot in FIG. 18B. If the cell is disassembled, and the inside of the separation channel is visually inspected, debris is observed to accumulate to the greatest degree in the first few mm of the ion path as shown in FIGS. 18C and 18D. This region correlates with the presence of strong fringing fields generated by the RF and DC potentials as shown in the simulations of both ions and charged particle trajectories in the entrance region of the cell in FIG. 19. The simulation shows a charged particle being deflected and striking the electrode at the entrance to the cell (1) due to the fringing fields, and an ion (2) passing through the entrance fields. It is likely that the fringing fields account for the removal of a large portion of this material. The cell is in the atmospheric ion source region and can be easily removed and replaced without breaking vacuum or even requiring the use of tools. Down time is only a few minutes and can be addressed by unskilled operators. Additionally, the ion beam in this region is not significantly affected by the accumulation of debris. This is because the trajectory of ions in this region is primarily controlled by strong gas flows so perturbations in the fields at the entrance do not significantly reduce analyte ion transmission or resolution.

The section headings used herein are for organizational purposes only and are not to be construed as limiting. While the Applicants' teachings are described in conjunction with various embodiments, it is not intended that the applicants' teachings be limited to such embodiments. On the contrary, the Applicants' teachings encompass various alternatives, modifications, and equivalents, as will be appreciated by those of skill in the art.

The invention claimed is:

1. A system for analyzing ions comprising:
an ion source;
a low resolution, high transmission ion mobility spectrometer for reducing contamination having an input end for receiving ions from the ion source and an output end, the ion mobility spectrometer having an internal operating pressure, electrodes, and at least one voltage source for providing DC and RF voltages to the electrodes;
a mass spectrometer in fluid communication with the ion mobility spectrometer for receiving the ions from the output end of ion mobility spectrometer; and
a controller operably coupled to the ion mobility spectrometer and configured to control the DC and RF voltages; and
wherein the ion mobility spectrometer is configured such that a ratio of a residence time of the ions through the ion mobility spectrometer to a product of gap height between electrodes of the ion mobility spectrometer and a maximum separation voltage applied to the electrodes of the ion mobility spectrometer being less than 0.002 second/(meter*volt).

2. The system of claim 1, wherein the spectrometer is configured such that the ratio of the residence time of the ions through the ion mobility spectrometer to the product of gap height between electrodes of the ion mobility spectrometer and the maximum separation voltage applied to the electrodes of the ion mobility spectrometer being less than 0.0015 second/(meter*volt).

3. The system of claim 1, wherein the residence time of the ions is less than 100 milliseconds.

4. The system of claim 1, wherein the gap height is between 0.02 and 5 millimeters.

5. The system of claim 1, wherein the separation voltage (SV) comprises an RF signal applied to the electrodes, and including a compensation voltage (CoV) comprised of a DC signal applied to the electrodes and wherein the RF and DC signals are configured to generate a fringing field in proximity of said input end of the ion mobility spectrometer effective to cause said ions having a selected mass to follow off-axis trajectories to collide with said electrodes in proximity to said input end.

6. The system of claim 1, further comprising selecting a transit time of the ions through the ion mobility spectrometer to facilitate transit of analytes of interest through the ion mobility spectrometer.

7. The system of claim 6, wherein the transit time is selected to provide transmission efficiency of greater than 50% for a broad mass range of ions.

8. The system of claim 1, wherein the ion mobility spectrometer comprises a differential mobility spectrometer or FAIMS spectrometer.

* * * * *